United States Patent
Smith et al.

(10) Patent No.: US 10,905,843 B2
(45) Date of Patent: Feb. 2, 2021

(54) HUMIDIFICATION OF RESPIRATORY GASES

(71) Applicant: Fisher & Paykel Healthcare Limited, Auckland (NZ)

(72) Inventors: Daniel John Smith, Auckland (NZ); Anthony James Newland, Auckland (NZ); Po-Yen Liu, Auckland (NZ); Stefan Leo Van Workum, Auckland (NZ); Ivan Chih-Fan Teng, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 380 days.

(21) Appl. No.: 16/070,516

(22) PCT Filed: Jan. 16, 2017

(86) PCT No.: PCT/NZ2017/050003
§ 371 (c)(1),
(2) Date: Jul. 16, 2018

(87) PCT Pub. No.: WO2017/126980
PCT Pub. Date: Jul. 27, 2017

(65) Prior Publication Data
US 2019/0076617 A1    Mar. 14, 2019

Related U.S. Application Data

(60) Provisional application No. 62/362,709, filed on Jul. 15, 2016, provisional application No. 62/280,076, filed on Jan. 18, 2016.

(51) Int. Cl.
*A61M 16/16*    (2006.01)
*A61M 16/00*    (2006.01)
(Continued)

(52) U.S. Cl.
CPC ........ *A61M 16/16* (2013.01); *A61M 16/0069* (2014.02); *A61M 16/024* (2017.08);
(Continued)

(58) Field of Classification Search
CPC ...... A61M 16/00; A61M 16/003–0012; A61M 2016/0015–0042; A61M 2016/01–026;
(Continued)

(56) References Cited

U.S. PATENT DOCUMENTS

| 8,453,643 B2 | 6/2013 | Sanchez et al. |
| 8,539,949 B2 | 9/2013 | Leone et al. |

(Continued)

FOREIGN PATENT DOCUMENTS

| EP | 2229973 B1 | 8/2012 |
| WO | WO 2003/048721 A2 | 6/2003 |

(Continued)

OTHER PUBLICATIONS

International Search Report dated Aug. 11, 2017, International Application No. PCT/NZ2017/050003, filed Jan. 16, 2017.

*Primary Examiner* — Timothy A Stanis
*Assistant Examiner* — Ned T Heffner
(74) *Attorney, Agent, or Firm* — Knobbe, Martens, Olson & Bear, LLP

(57) ABSTRACT

A respiratory assistance system including a humidification apparatus used for delivery of heated and humidified gases to a patient includes a humidification chamber with an associated heater and sensor, an inspiratory conduit with an associated heater and sensor, and an unheated patient interface, such as a face mask. A controller of the humidification apparatus is configured to determine a gas source and change the set point accordingly to maintain patient comfort regardless of the humidity level of the gas source.

26 Claims, 19 Drawing Sheets

(51) Int. Cl.
*A61M 16/08* (2006.01)
*A61M 16/10* (2006.01)

(52) U.S. Cl.
CPC ...... *A61M 16/026* (2017.08); *A61M 16/0891* (2014.02); *A61M 16/109* (2014.02); *A61M 16/1095* (2014.02); *A61M 16/161* (2014.02); *A61M 2016/0036* (2013.01); *A61M 2016/0039* (2013.01); *A61M 2205/3368* (2013.01)

(58) Field of Classification Search
CPC ... A61M 2016/10–1045; A61M 2016/12–127; A61M 2016/14–147; A61M 2016/16–168; A61M 2016/18–186; A61M 11/00; A61M 11/04–044; A61M 11/065; A61M 15/085–15/088
See application file for complete search history.

(56) References Cited

U.S. PATENT DOCUMENTS

| | | |
|---|---|---|
| 9,387,297 B2 | 7/2016 | Leone et al. |
| 2003/0106554 A1* | 6/2003 | de Silva .............. A61M 16/122 128/204.22 |
| 2007/0265877 A1 | 11/2007 | Rice et al. |
| 2007/0272239 A1 | 11/2007 | Aylsworth et al. |
| 2008/0308100 A1 | 12/2008 | Pujol et al. |

FOREIGN PATENT DOCUMENTS

| | | |
|---|---|---|
| WO | WO 2008/091164 A1 | 7/2008 |
| WO | WO 2011/159393 | 12/2011 |
| WO | WO 2014/052983 A1 | 4/2014 |

\* cited by examiner

HUMIDIFICATION OF RESPIRATORY GASES

CROSS-REFERENCE TO RELATED APPLICATIONS

This application claims priority to U.S. Provisional Application No. 62/280,076, filed Jan. 18, 2016 and U.S. Provisional Application No. 62/362,709 filed Jul. 15, 2016, each of which is hereby incorporated by reference in its entirety.

BACKGROUND

Field of the Invention

The present invention generally relates to humidifying respiratory gases. More particularly, the present disclosure relates to a respiratory assistance system and a method for operation of a respiratory assistance system that controls the temperature and humidity levels of respiratory gases to increase patient comfort and to improve respiratory assistance system performance.

Description of the Invention

A respiratory assistance system including a gas source and a humidification apparatus may be used to deliver heated and humidified respiratory gases to a patient through a conduit and a patient interface. During unassisted inspiration, the upper airway heats and humidifies inspired gases to a humidity condition of 100% relative humidity at a body temperature of 37° C., or 44 mg/L absolute humidity. The humidification apparatus may be configured to heat and humidify the respiratory gases to a humidity condition such that the respiratory gases reaching the patient's lungs mimic, as closely as possible, the gases received during unassisted inspiration.

SUMMARY

Certain aspects, advantages and novel features of the present disclosure are described herein. It is to be understood that not necessarily all such advantages may be achieved in accordance with any particular embodiment of the present disclosure. Thus, the features, aspects, and advantages of the present disclosure may be embodied or carried out in a manner that achieves or selects one advantage or group of advantages as taught herein without necessarily achieving other advantages as may be taught or suggested herein.

According to a first aspect of the present disclosure, there is provided a respiratory assistance system for delivery of heated and humidified gases to a patient via a patient interface from a gases source through an inspiratory conduit and a humidification chamber, the respiratory assistance system comprising: a chamber heater configured to heat and humidify a flow of respiratory gases; and a controller comprising one or more hardware processors configured to: determine one or more characteristics of respiratory gases; and determine a type of gases source based on the determined characteristic or respiratory gases.

In some embodiments, the respiratory assistance system comprises a patient interface configured to deliver a flow of respiratory gases received from a gases source. In some such configurations, the respiratory assistance system comprises an inspiratory conduit configured to be in fluid communication with the patient interface and the gases source. In some such configurations, the respiratory assistance system comprises a humidification chamber comprising a chamber inlet, a chamber outlet, and a gases flow path between the chamber inlet and the chamber outlet, the chamber inlet configured to be in fluid communication with the gases source and the chamber outlet configured to be in fluid communication with the inspiratory conduit, the humidification chamber configured to hold a volume of liquid.

In some embodiments, the controller is configured to generate an indicator corresponding to the determined type of gases source for communication to a user.

In some embodiments, the controller is configured to control a set point temperature associated with the chamber heater based on the determined type of gases source. In some such configurations, controlling the set point temperature comprises modifying a representation of the set point temperature in a hardware memory. In some such configurations, the controller is configured to lower the set point temperature based on the determination of the type of gases source to be an air entraining gases source. In some such configurations, the controller is configured to generate an indicator corresponding to the set point temperature for communication to a user.

In some embodiments, the characteristics of respiratory gases comprises at least one of: a mean flow rate, a breathing pattern, a bias flow rate, a reverse flow detection, a rebreathing detection.

In some embodiments, the determination of the type of gases source comprises detecting a hardware component attached to the humidification chamber. In some such configurations, the hardware component is an expiratory circuit or an expiratory conduit. In some such configurations, the detection of the expiratory circuit is based on a characteristic signal comprising at least one of: a voltage measurement, or an impedance measurement, or a resistance measurement.

In some embodiments, the determination of the type of gases source comprises detecting a behaviour of the flow of respiratory gases based on the determined one or more characteristics of the respiratory gases. In some such configurations, the behaviour comprises a detection of a breathing pattern, a detection of bias flow, or a detection of rebreathing. In some such configurations, the detection of the breathing pattern comprises monitoring flow movements or pressure changes and comparing the monitored flow movements or pressure changes with a threshold. In some such configurations, the detection of bias flow comprises measuring a raw flow measurement from a flow sensor and comparing the raw flow measurement with a bias threshold. In some such configurations, the determination of the type of gases source may comprise comparing a bias flow rate with a mean flow rate. In some such configurations, the controller is configured to determine a bias flow rate based on a rate of change of flow. In some such configurations, the controller is configured to determine the bias flow rate by deriving a rate of change of flow from flow rate measurements, determining an average flow and performing a first check to confirm a bias flow, wherein the first check involves determining if the rate of change is 0 and the flow is less than the average flow.

In some embodiments, the detection of rebreathing comprises determining a flow profile detected at an outlet flow sensor and an inlet flow sensor; and comparing the flow profiles with a predetermined flow profile.

In some embodiments, the detection of rebreathing comprises extracting a first flow profile at an inlet flow sensor and a second flow profile at an outlet flow sensor; and comparing the first flow profile with the second flow profile.

In some embodiments, the detection of rebreathing comprises detecting an inspiratory phase and an expiratory phase; and comparing a length of the expiratory phase with a length of the inspiratory phase.

In some embodiments, the detection of rebreathing comprises correlating an inspiratory phase breathing pattern with an expiratory phase breathing pattern.

In some embodiments, the respiratory assistance comprises an inlet temperature sensor, wherein the one or more characteristics of respiratory gases comprises a temperature measurement from the inlet temperature sensor, and wherein the controller is configured to determine the type of gases source based on comparing the temperature measurement from the inlet sensor with one or more thresholds. In some such configurations, if the inlet temperature is less than the threshold denotes a non air entraining ventilator, and if the inlet gases temperature is greater than the threshold denotes an air entraining ventilator.

According to a second aspect, there is provided a respiratory assistance system comprising: a controller comprising one or more hardware processors and a memory; and a chamber heater; wherein the controller is configured to: detect a rebreathing flow pattern; determine a gases source or an operating condition based on the detection of the rebreathing flow pattern; and control an operating parameter based corresponding to the chamber heater on the determination of the gases source.

In some embodiments, the detection of the rebreathing flow pattern may comprise correlating measurements from an inlet sensor and an outlet sensor. In some such configurations, the inlet sensor and the outlet sensor comprise one or more flow sensors configured to detect a flow pattern or flow signal, and wherein the detection of the rebreathing flow pattern comprises correlating the flow pattern or flow signal. In some such configurations, the operating parameter is a chamber outlet temperature set point. In some such configurations, the flow pattern or flow signal comprises one or more power dissipation values, and wherein the one or more flow sensors comprise a heated bead flow sensor. In some such configurations, the gases source comprises an air entraining ventilator or a non-air entraining ventilator.

According to a third aspect, there is provided a controller comprising one or more hardware processors coupled to a respiratory assistance system, the controller configured to automatically determine a configuration of the respiratory assistance system, the controller comprising: a hardware memory; a user interface configured to receive an input from a user; and one or more hardware processors coupled to a plurality of hardware components of the respiratory assistance system; wherein the one or more hardware processors are configured to detect the received user input and automatically confirm the operational configuration of the system matches the received user input based on one or more sensor inputs from at least one sensor or the hardware components.

In some embodiments, the one or more hardware processors are configured to select a default mode based on no input received from the user. In some such configurations, the one or more hardware processors are configured to select a safety mode prior to confirmation of the operational configuration. In some such configurations, the one or more hardware processors are configured to control a heater plate temperature of a heater plate based on a first temperature measurement from the outlet temperature sensor and a second temperature measurement corresponding to the outlet temperature set point.

According to a fourth aspect, there is provided a respiratory assistance system for delivery of heated and humidified gases to a patient, the respiratory assistance system comprising: a gas source configured to provide a flow of respiratory gases; a patient interface configured to deliver the flow of respiratory gases to the patient; an inspiratory conduit configured to be in fluid communication with the patient interface; a humidification chamber configured to hold a volume of liquid, the humidification chamber including a chamber inlet, a chamber outlet, and a gases flow path between the chamber inlet and the chamber outlet, the chamber inlet configured to be in fluid communication with the gas source and the chamber outlet configured to be in fluid communication with the inspiratory conduit; a chamber heater configured to heat the volume of liquid and the flow of respiratory gases in the gases flow path within the humidification chamber so as to heat and humidify the flow of respiratory gases; and a controller configured to: determine a gases characteristic of the flow of respiratory gases provided by the gas source; determine whether to change a first temperature, based at least in part on the determined gases characteristic; and determine an amount of power to provide to the chamber heater, based at least in part on the determined gases characteristic and at least in part on the first temperature.

In some embodiments, the respiratory assistance system comprises a flow rate sensor, wherein said controller is configured to change the first temperature based at least in part on a measurement from the flow rate sensor. In some such configurations, the controller is configured to: detect a signal from a heating element corresponding to an expiratory conduit; and change the first temperature based at least in part on the detected signal. In some such configurations, the controller is further configured to: receive user input from a display; and change the first temperature based at least in part on the user input.

The respiratory assistance system may comprise a temperature sensor, wherein the controller is further configured to: receive a measurement from the temperature sensor; and change the first temperature based at least in part on the received measurement from the temperature sensor.

The respiratory assistance system may comprise a humidity sensor wherein the controller is further configured to: receive a measurement from the humidity sensor; and change the first temperature based at least in part on the received measurement from the humidity sensor.

According to a fifth aspect, there is provided a respiratory assistance system configured to automatically determine which of a plurality of optional configuration components and settings are used with the respiratory assistance system, the system comprising: a plurality of optional hardware components, wherein each component is configured to be connectable with the respiratory assistance system; and a hardware processor configured to analyse operational characteristics based on one more inputs from at least one sensor or optional hardware component attachments and determine a desired operational configuration based on the analysis.

According to a sixth aspect, there is provided a respiratory assistance system configured to automatically determine which of a plurality of optional configuration components and settings are used with the respiratory assistance system, the system comprising: a plurality of optional hardware components, wherein each component is configured to be connectable with the respiratory assistance system; a user interface configured to receive an input from a user; and a hardware processor configured to detect the received user input and automatically confirm that an operational configuration of the respiratory assistance system matches with the received user input based on one more inputs from at least one sensor or optional hardware component attachments.

In some embodiments, at least one of the optional hardware components comprises an expiratory heater wire. In some such configurations, the hardware processor is configured to detect a signal characteristic from the expiratory heater wire to determine a status of connection of the expiratory heater wire. In some such configurations, the signal characteristic comprises at least one of a voltage measurement or a resistance measurement.

According to a seventh aspect, there is provided a method for determining a type of gases source comprising: determining one or more characteristics of respiratory gases; and determining a type of gases source based on the determined characteristics of respiratory gases.

In some embodiments, the method can include any of the features and/or steps of the first to sixth aspects to determine the characteristics of respiratory gases.

According to an eighth aspect, there is provided a respiratory assistance system for delivery of heated and humidified gases to a patient, the respiratory assistance system comprising: a patient interface configured to deliver a flow of respiratory gases received from a gases source; an inspiratory conduit configured to be in fluid communication with the patient interface and the gases source; a humidification chamber comprising a chamber inlet, a chamber outlet, and a gases flow path between the chamber inlet and the chamber outlet, the chamber inlet configured to be in fluid communication with the gases source and the chamber outlet configured to be in fluid communication with the inspiratory conduit, the humidification chamber configured to hold a volume of liquid; a chamber heater configured to heat the volume of liquid and the flow of respiratory gases in the gases flow path within the humidification chamber so as to heat and humidify the flow of respiratory gases; and a controller comprising one or more hardware processors configured to: determine one or more characteristics of respiratory gases; and determine a type of gases source based on the determined characteristic of respiratory gases.

In some embodiments, the method of the seventh aspect is configured to utilize any of the features of the first to sixth aspects.

For purposes of summarising the disclosure and the advantages achieved over the prior art, certain objects and advantages have been described herein. It is to be understood that not necessarily all such objects or advantages need to be achieved in accordance with any particular embodiment. Thus, for example, those skilled in the art will recognise that the disclosed configuration or configurations may be embodied or carried out in a manner that achieves or optimises the one advantage or group of advantages as taught or suggested herein without necessarily achieving other advantages as may be taught or suggested herein. All of these embodiments are intended to be within the scope of the present disclosure.

BRIEF DESCRIPTION OF THE DRAWINGS

These and other features, aspects, and advantages of the present disclosure will be described with respect to the following figures, which are intended to illustrate and not to limit the preferred embodiments.

DETAILED DESCRIPTION

Figure 1:
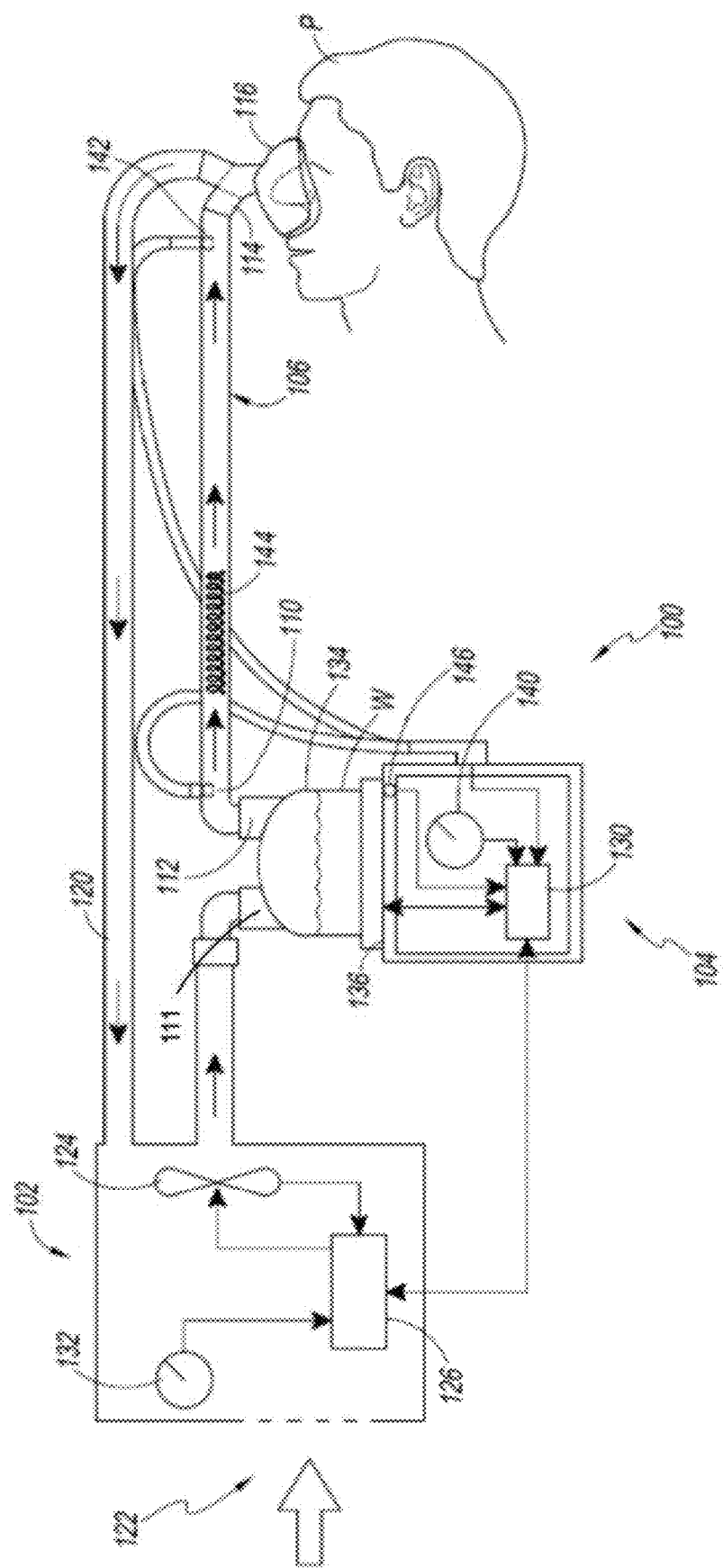
FIG. 1 illustrates a diagram of a respiratory assistance system according to an embodiment of the present disclosure.

FIG. 1 shows a schematic of an example respiratory assistance system 100. As illustrated, the respiratory assistance system 100 includes a humidification apparatus 104, a gas source 102, a patient interface 116, and an inspiratory conduit 106 configured to transport respiratory gases from the humidification apparatus 104 to the patient interface 116. In some embodiments, the gas source 102 and the humidification apparatus 104 may be co-located, within the same housing, and/or include a single apparatus. In some embodiments, the respiratory assistance system 100 includes an expiratory conduit 120 configured to transport gases from the patient interface 116 to the gas source 102 and a wye-piece 114 configured to connect the inspiratory conduit 106 and the expiratory conduit 120 to the patient interface 116. In some embodiments, the respiratory assistance system 100 does not include the expiratory conduit 120 and thus may include an exhalation port (not shown) configured to connect the inspiratory conduit 106 to the patient interface 116, as would be understood by a person of skill in the art from the present disclosure. Accordingly, the respiratory assistance system 100 can include at least two configurations: a first configuration that includes the expiratory conduit 120 and a second configuration that does not include the expiratory conduit 120. In some embodiments, the operating parameters of the respiratory assistance system 100 may need to be adjusted depending on the configuration.

As illustrated, the gas source 102 includes a gas delivery mechanism 124, such as a blower or a turbine. The gas source 102 may also include other mechanical mechanisms to deliver or push a flow of respiratory gases to the humidification apparatus 104. The gas source 102 in the illustrated embodiment of FIG. 1 is an example of a room or ambient air entraining gas source. The gas source 102 may include an inlet 122 through which ambient air is drawn into the gas source 102, e.g., by the gas delivery mechanism 124. In some embodiments, the gas source 102 may include a controller 126 configured to control the operation of the blower 124. In some embodiments, the gas source 102 may include a user interface 132 that can provide information regarding user input to the controller 126. The controller 126 can control the operation of the blower 124 based on information provided by the user interface 132 and/or based on other information, for example but not limited to, feedback from the blower 124, such as from a sensor associated with the blower 124. In some embodiments, instead of drawing ambient air, the inlet 122 can be connected to a supply of dry gas, for example, a gas canister or tank. This type of ventilators can be referred to non-entraining ventilators and may be controlled by one or more valves such as proportional valves. The valve or valves may be controlled by a controller. The non-entraining ventilator may also be connected to a humidifier 104 as shown in FIG. 1, and include an expiratory limb 120.

The humidification apparatus 104 may include a humidification chamber 134 and a chamber heater 136. The humidification chamber 134 may be configured to hold a volume of water W or other suitable liquid. The chamber heater 136 may be configured to heat the volume of water W and respiratory gases within the humidification chamber 134, which may increase the temperature of the respiratory gases and may create vapor from the volume of water W that is taken up by the respiratory gases. In some embodiments, the humidification chamber 134 may include a chamber inlet 111 and a chamber outlet 112. In some embodiments, the inspiratory conduit 106 may be configured to be connected to the chamber outlet 112, such that heated and humidified respiratory gases may be transported by the inspiratory conduit 106 from the humidification chamber 134 to the patient interface 116 and then delivered to a patient P. In some embodiments, gases exhaled by the patient P into the patient interface 116 may be returned by the expiratory conduit 120 to the gas source 102. In some embodiments, the respiratory assistance system 100 does not include the expiratory conduit 120 and thus gases exhaled by the patient P into the patient interface 116 may be vented to the atmosphere through a connector with an exhalation port (not shown).

In some embodiments, the humidification apparatus 104 may include a controller 130 that can control the operation of the chamber heater 136. The humidification apparatus 104 may also include a user interface 140 for providing and/or receiving information regarding user input to the controller 130. The humidification apparatus 104 may further include an ambient sensor 146. The ambient sensor 146 may measure a characteristic of the ambient air near the location of the ambient sensor 146, such as a temperature of the ambient air. In an embodiment, the ambient sensor 146 is a temperature sensor located at or near the inlet 111. The temperature sensor at the inlet 111 can measure both temperature and flow rate (as discussed below) of the air coming in from the gas source 102. This measurement can provide indication of ambient conditions. The controller 130 may receive information regarding a characteristic of the ambient air near the location of the ambient sensor 146 from the ambient sensor 146. The controller 130 may be configured to control the operation of the chamber heater 136 based on information provided by the user interface 140, based on information provided by the ambient sensor 146, and/or based on other information, for example but not limited to, feedback from the chamber heater 136, such as from a sensor associated with the chamber heater 136. In particular, the controller 130 may be configured to determine an amount of power, or a power duty cycle, to provide to the chamber heater 136 such that the chamber heater 136 delivers a desired amount of heat to respiratory gases and the volume of water W within the humidification chamber 134. Additionally and/or alternatively, one or more.

In some embodiments, the respiratory assistance system 100 may include one or more outlet sensors 110 that are associated with the chamber outlet location 112. The one or more outlet sensors 110 may also be located at or near the outlet passage as shown with numeral 112 for the chamber outlet location in the illustrated embodiment. Additionally and/or alternatively, the respiratory assistance system 100 may include one or more sensors located at or near the chamber inlet 111 in some embodiments. The inlet sensors can also include a temperature sensor and a flow sensor. In some embodiments, only one sensor at the inlet 111 is used for measuring both temperature and flow as discussed in detail below. In some embodiments, the one or more inlet sensors could be located at any location from gas source 102 to humidification chamber 134. The one or more outlet sensors 110 and the one or more inlet sensors may be integrated with the humidification chamber in some embodiments. The location of the sensors may vary some of the readings and thresholds discussed below. In an embodiment, the outlet sensors 110 include two sensors: a temperature sensor and a flow sensor. The temperature sensor can be a heated bead sensor or a thermistor or a heated thermistor. In some embodiments, the heated bead sensor can also be used as a flow sensor. Accordingly, in some embodiments, there is a single sensor at or near the outlet 112. Other types of temperature sensors and flow sensors that can work in a respiratory assistance system 100 may also be used. The outlet sensor(s) 110 may be located at the chamber outlet 112, at the inspiratory conduit 106 near the connection between the chamber outlet 112 and the inspiratory conduit 106, or at another suitable location. The outlet sensor(s) 110 may measure a characteristic of respiratory gases flowing past the location of the outlet sensor(s) 110, such as a temperature of the respiratory gases or the flow rate. The controller 130 may receive information from the outlet sensor(s) 110 regarding a characteristic of respiratory gases flowing past the location of the outlet sensor 110. The controller 130 may be configured to control the operation of the chamber heater 136 based on information provided by the outlet sensor(s) 110, instead of or in addition to other sources of information as previously described.

Respiratory gases flowing through the inspiratory conduit 106 may lose heat through the walls of the inspiratory conduit 106, which may reduce the temperature of the respiratory gases and may cause condensation to form within the inspiratory conduit 106. In some embodiments, the inspiratory conduit 106 may include a conduit heater 144 configured to heat the inspiratory conduit 106 to reduce or prevent this loss of heat. The controller 130 may be configured to control the operation of the conduit heater 144 based on one or several sources of information as previously described. In particular, the controller 130 may be configured to determine an amount of power, or a power duty cycle, to provide to the conduit heater 144 such that the conduit heater 144 delivers a desired amount of heat to the inspiratory conduit 106.

In some embodiments, the respiratory assistance system 100 may include one or more conduit sensors 142 that are associated with the inspiratory conduit 106. The conduit sensor(s) 142 may be located at the inspiratory conduit 106 near the connection between the inspiratory conduit 106 and the wye-piece 114, at the connection between the inspiratory conduit 106 and the patient interface 116 if the inspiratory conduit 106 is connected directly to the patient interface 116, or at the wye-piece 114 or the patient interface 116. The conduit sensor(s) 142 may measure a characteristic of respiratory gases flowing past the location of the conduit sensor 142, such as a temperature of the respiratory gases. In an embodiment, the conduit sensor 142 includes a temperature sensor. The conduit sensor 142 can also include a separate flow sensor. In an embodiment, the conduit sensor 142 includes an integral flow and temperature sensor that is capable of measuring both the temperature and flow rate as described herein. The controller 130 may receive information regarding a characteristic of respiratory gases flowing past the location of the conduit sensor 142 from the conduit sensor 142. In an embodiment, the controller 130 derives the flow rate of respiratory gases flowing past the conduit sensor 142. The controller 130 may be configured to control the operation of the conduit heater 144, and/or the operation of the chamber heater 136, based on information received from the conduit sensor 142, instead of or in addition to other sources of information as previously described.

Respiratory gases may also lose heat through the walls of the patient interface 116, the wye-piece 114, and any other respiratory system component that may connect the patient interface 116 to the inspiratory conduit 106. In some embodiments, one or more of the patient interface 116, the wye-piece 114, and any other respiratory system component that may connect the patient interface 116 to the inspiratory conduit 106 may include an associated heater and/or an associated sensor (not shown). In some such embodiments, the controller 130 may receive information from such an associated sensor regarding a characteristic of respiratory gases flowing past the location of the sensor. In some such embodiments, the controller 130 may use information received from such an associated sensor to control the operation of the respective associated heater.

In some embodiments, one or more of the patient interface 116, the wye-piece 114, and any other respiratory system component that may connect the patient interface 116 to the inspiratory conduit 106 may not include an associated heater and/or an associated sensor. In some such embodiments, the controller 130 may use an estimate of the heat lost by respiratory gases flowing through unheated respiratory system components to control other heaters associated with the humidification apparatus 104, such as the chamber heater 136 and/or the conduit heater 144. In some such embodiments, the controller 130 may calculate such a heat loss estimate for unheated respiratory system components based on other received information, such as, but not limited to, information received from the outlet sensor 110, the conduit sensor 142, the ambient sensor 146, and/or the user interface 140, and/or based on information retrieved from a data storage device (not shown). The data received from the sensors described herein can also be stored in the data storage device.

The humidification apparatus 104 may be used in the respiratory assistance system 100 to deliver heated and humidified respiratory gases to the patient P for multiple types of respiratory therapies, including but not limited to invasive ventilation therapy, non-invasive ventilation therapy, high flow therapy, and positive airway pressure therapy. The humidity conditions of the respiratory gases provided to the humidification apparatus 104 by the gas source 102 may vary. For example, the type of the gas source 102 used in the respiratory assistance system 100 may depend on the type of respiratory therapy, respiratory system configurations, location of use (such as home or hospital), or availability of different gas supplies. Gases from different supplies may have different characteristics, including temperature and humidity. Ambient air has higher humidity than gas obtained from a compressed gas tank or bottle. In some embodiments, it may be advantageous to adjust the operating parameters of the respiratory assistance system 100 using a control system 220 (described below) such that the patient receives comfortable care regardless of the supply gas characteristics. The control system may be able to automatically, or semi-automatically, adjust operating parameters based on an inference of whether the supply gas is dry or ambient. The operating parameters may include temperature set points corresponding to heater elements discussed above. The following describes some of the different configurations of the respiratory assistance system 100.

The configuration of the gas source 102 can correspond to a type of supply gas used by the respiratory assistance system 100. Accordingly, to infer the supply gas characteristics (such as dry gases or ambient air), the control system 220 depicted in FIG. 2 can determine a type of the gas source 102 used in the respiratory assistance system 100. Examples of types of the gas source 102 include either room air entraining gases source or a non-entraining gases source. Air entraining gases sources include a turbine ventilator, a blower, or any other form of gases propulsion apparatus. The non-air entraining ventilator receives gases from a wall gases source, such as a pressurized tank or a pump, or a portable gases sources such as a gas bottle. Non-entraining ventilators can include valves or other suitable components to control delivery of gases to the humidifier chamber 104. In some embodiments, the processes discussed herein are independent of the supply pressure. In some embodiments, the gas source 102 includes a room entraining ventilator, such as a turbine ventilator or a blower. In such embodiments, the gas source 102 generally includes an impeller to entrain an ambient gas supply. In an embodiment, the difference between a turbine ventilator and a blower is that a turbine ventilator may pulse the inspiratory gas flow and thus need pressure feedback. In contrast, a blower may provide a continuous flow of inspiratory gases without requiring any pressure feedback. When the gas source 102 includes a blower, there may be no pulsing, no pressure feedback, and no exhalation port. This setup may be used in high flow therapy or non-invasive therapy. Accordingly, the control system 220 can use a lack of pressure feedback or no pulsing to determine the type of gas source 102.

As discussed above, the control system 220 can identify the setup based on the components included or not included in the respiratory assistance system 100. For example, room air entraining ventilators are often used in a single limb ventilation. In single limb ventilation, there is no expiratory conduit and the humidification system includes a single inspiratory limb/conduit. The patient receives respiratory gases via the inspiratory limb. In a non-invasive ventilation therapy, an exhalation port can allow for venting of exhaled gases. While in a high flow therapy, no exhalation port may be required. Alternatively, the patient may be treated with or supplied using a dual limb ventilation system as illustrated in FIG. 1. A dual limb ventilator includes an inhalation limb or circuit or conduit and an exhalation limb or conduit or circuit. An example of the dual limb ventilation is shown in FIG. 1. Dual limb ventilation may be used on intubated patients to supply invasive therapy. The single limb arrangement can be used for non-invasive therapy, such as for example delivery of gases by a mask or a nasal cannula or other suitable non-invasive patient interfaces.

Both invasive and non-invasive therapies can be supplied using a room air entraining ventilator or a non-entraining ventilators, such as a wall source. For non-invasive therapy, the system can use either dual limb or single limb. Furthermore, for non-invasive therapy, the respiratory assistance system 100 may use a room air entraining ventilator (that entrains ambient air) or a wall source (non-entrained dry gases). Thus, in some embodiments, it is advantageous to determine the gases source and vary the supplied humidity accordingly to achieve an optimal humidity delivery. Without detection of gases source, the patient may not receive optimal therapy in some instances. Further gases source detection may also be used by the control system 220 to ensure that a predetermined humidity is delivered to the patient and to reduce condensation within the inspiratory conduit 106. Condensation can deteriorate patient's comfort and prolonged presence may lead to skin damage. Thus, detection of gases source may be important in some instances to optimize humidity delivery. Therefore, the control system discussed herein identifies the gases source and appropriately controls the heating components of the respiratory assistance system 100 in order to ensure optimal humidity is delivered to the patient.

In some embodiments, it is possible that when ambient air is used, the respiratory assistance system 100 will not include the expiratory conduit 120. When the gas source 102 includes a room air entraining ventilator such as a turbine ventilator, the respiratory assistance system 100 can include an exhalation port at the patient end to allow for venting of expiratory gases. Furthermore, pressure feedback may be provided by a pressure line attached to a pressure port on the exhalation port or adjacent to the exhalation port. The gases may not be vented via the exhalation port initially but may travel back towards the humidification chamber 134 upon exhalation. Thus, if such a gas flow pattern can be detected, it is likely that the respiratory assistance system 100 uses ambient air. Accordingly, the above system conditions may be used by the control system 220 to determine whether the respiratory assistance system 100 is using ambient air and optionally the type of therapy delivered.

In another embodiment, the gas source 102 can use a dry gas supply. When using a dry gas supply, the gas source 102 will likely include a non-entraining ventilator. Further, the respiratory assistance system 100 may include the expiratory conduit 120 with the non-entraining ventilator. The valves can control movement of inspiratory and expiratory gases from a wall source, for example, in a non-entraining ventilator. Therefore, it is unlikely that exhaled gases from the patient will return to the chamber end of the tube or conduit because exhalation is controlled by the valves. Accordingly, the control system 220 can receive pressure feedback via the expiratory conduit 120. This setup may be used for either non-invasive ventilation therapy or invasive ventilation therapy. It is more common that a non-entraining ventilator with a dual limbed system is used for invasive therapies. The control system 220 can detect the pressure feedback and/or expiratory limb to determine that the respiratory assistance system 100 includes a non-entraining ventilator and may accordingly be using a dry gas supply.

As discussed above, the type of the gas source 102 may also be a function of the therapy delivered by the respiratory assistance system 100, which can include but is not limited to: invasive ventilation therapy, non-invasive ventilation therapy, and high flow therapy. The age of the patient may also be a factor. For example, for an adult patient receiving invasive ventilation therapy, it is likely that the respiratory assistance system 100 includes the expiratory conduit 120 and uses a dry gas supply. For an adult patient receiving non-invasive ventilation therapy, it is likely that the respiratory assistance system 100 does not include the expiratory conduit 120, but either of a dry gas supply or ambient air may be used. When an adult patient receives high flow therapy, it is likely that the respiratory assistance system 100 does not include the expiratory conduit 120. For high flow therapy, typically ambient air is used, but high output humidity may be needed due to the high flows that may be used for this therapy. Additionally, supplemental oxygen from a dry gas supply may sometimes be mixed with ambient air for high flow therapy, resulting in a delivered gas mixture that is more humid than gas from a dry gas supply but less humid than ambient air.

For infants, invasive ventilation therapy may require a dry gas supply, and the respiratory assistance system 100 is likely to include the expiratory conduit 120. Additionally, for infants receiving Bubble CPAP (Continuous Positive Airway Pressure) therapy, a mixture of dry gas and entrained ambient air may be used as a gas supply. Further, for infants receiving high flow therapy, it is likely a dry gas supply is used and the respiratory assistance system 100 likely does not include the expiratory conduit 120. The above predetermined parameters for each type of therapy can be saved in a memory and used by the control system 220 to determine a likelihood that a particular type of gas supply is used.

Figure 2:
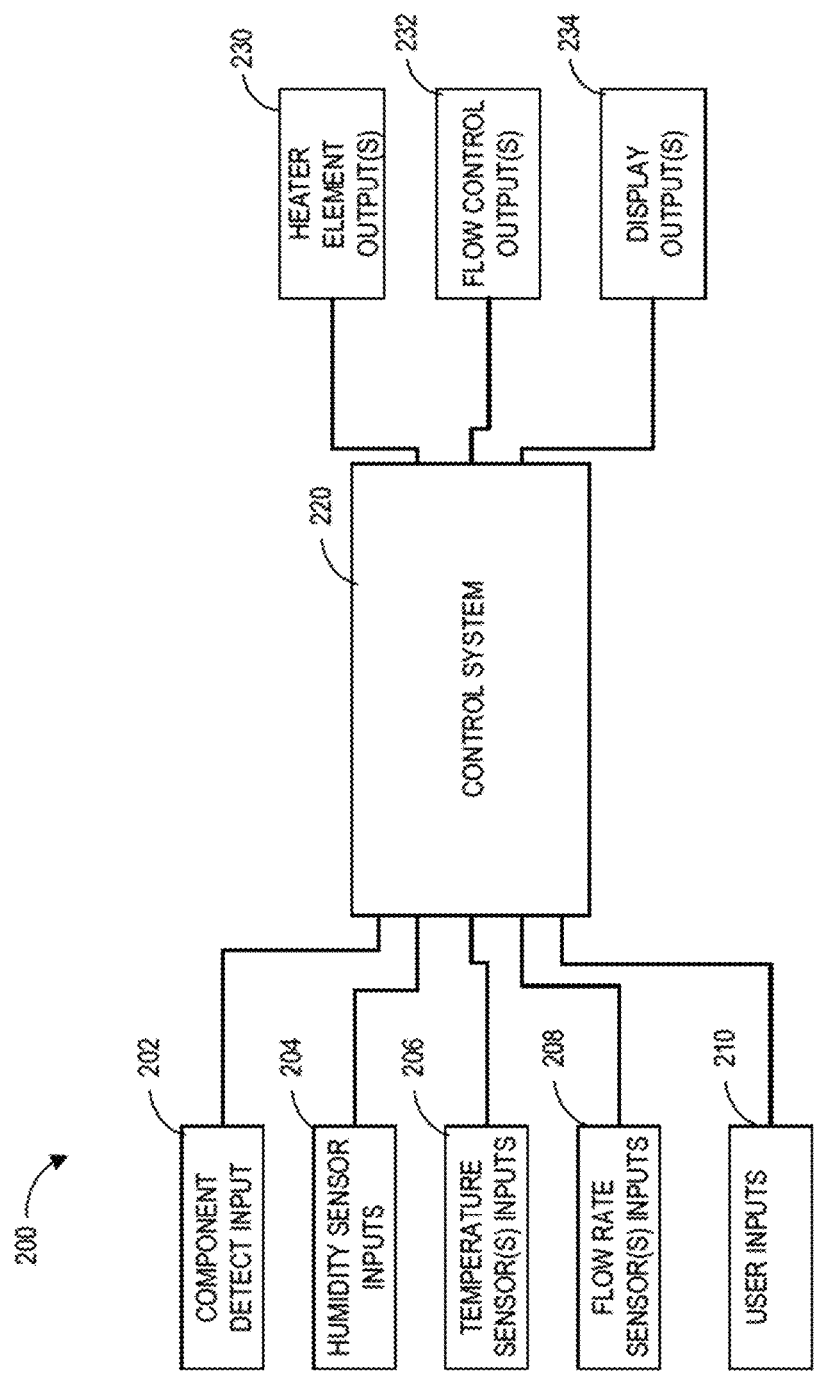
FIG. 2 illustrates a block diagram of a control system interacting with and/or providing control and direction to components of a respiratory assistance system according to an embodiment of the present disclosure.

FIG. 2 illustrates an embodiment of a control system 220 for detecting the input conditions of the gas source 102 and automatically, or semi-automatically, controlling the components of the respiratory assistance system 100 described above to change the output conditions of the gas delivered to the patient. In an embodiment, the control system 220 infers supply gas conditions at the gas source 102 based on the measured output gas conditions leaving the humidification chamber 134. The control system 220 can determine output gas conditions based on available sensor data. In some embodiments, the control system 202 receives a component detection input 202 from a heater adapter, a humidity sensor input 204 from an optional humidity sensor, a temperature sensor input 206 from a temperature sensor, a flow rate sensor input 208 from a flow rate sensor, and a user input 210 from the user interface 140. The sensors can be placed in one or more locations in the respiratory assistance system 100. For example, the humidity sensor can be located near the chamber inlet 111 or any location before the humidification chamber 134. In some embodiments, the humidity sensor can also be placed near the chamber outlet 112 instead of or in addition to the chamber inlet 111. The temperature sensor can also be located near the chamber outlet 112 or any other location along the path of the gas. In an embodiment, the temperature sensor is located in the humidification chamber 134. In some embodiments, the control system 220 receives a flow rate sensor input 208 from a pressure sensor instead of or in addition to the flow rate sensor input 208 from the flow sensor. In an embodiment, the flow rate is estimated from two temperature sensors.

The control system 220 can generate outputs, including outputs configured to control operation of components of the respiratory assistance system 100, based on the inputs received. In some embodiments, the control system can generate a heater element output 230 so as to change a temperature set point of one of the heating elements, such as the chamber heater 136, to control the output conditions of the gas delivered to the patient. The control system 220 can also change the operation or duty cycle of the heaters described above. In some embodiments, the control system 220 does not require direct communication between the humidification apparatus 104 and the gas source 102 for determination of the input conditions. The control system 220 can also generate a flow control output so as to change flow control and generate output 234 to a display.

Figure 9:
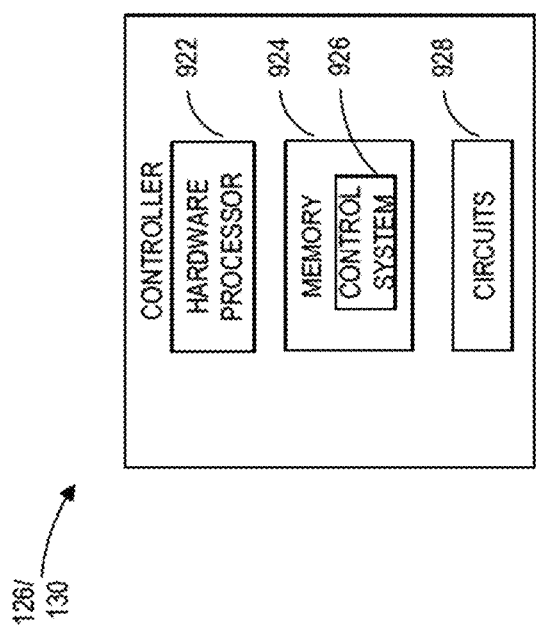
FIG. 9 illustrates a block diagram of a controller according to an embodiment of the present disclosure.

The control system 220 can include programming instructions described herein for detection of input conditions and control of output conditions. The programming instructions can be stored in a memory 924 of the controller 126, 130 as shown in FIG. 9. In some embodiments, the programming instructions correspond to the processes and functions described herein. The control system 220 can be executed by a hardware processor 922 of the controller 126, 130. The programming instructions can be implemented in C, C++, JAVA, or any other suitable programming languages. In some embodiments, some or all of the portions of the control system 220 can be implemented in application specific circuitry 928 such as ASICs and FPGAs.

As illustrated in FIG. 2, the control system 220 can receive inputs from multiple components of the respiratory assistance system 100. Not all of the inputs 202-210 shown in FIG. 2 may be present. Depending on the configuration, some of the components corresponding to the inputs 202-210 may not be included in the respiratory assistance system 100. For example, a humidity sensor is not included or available in many instances. Lack of input itself can be used by the control system 220 to determine the system conditions.

As discussed above, a humidity sensor can be positioned at or near the chamber inlet 111. In an embodiment, a humidity sensor can also be added to the chamber outlet 112 in addition to or instead of the humidity sensor at the chamber inlet 111. Adding a humidity sensor at the chamber outlet 112 may simplify determination of temperature set point or how much additional power is required to add sufficient humidity to the supply gas. However, design considerations may limit the usage of a humidity sensor at the chamber outlet 112. For example, a humidity sensor may malfunction in the presence of condensation and may also perform poorly at higher humidity. Accordingly, some of the embodiments described herein advantageously determine a temperature set point without having direct measurement of humidity level of the gases at the chamber outlet 112. Humidity sensors can also be expensive, need cleaning, and may be less durable. Accordingly, the control system 220 can use temperature as a proxy for humidity in some embodiments.

In some embodiments, the control system 220 automatically detects the components connected in the respiratory assistance system 100 from the input signals 202. For example, the control system 220 can automatically identify whether the respiratory assistance system 100 includes the expiratory conduit 120. To determine whether the respiratory assistance system 100 includes the expiratory conduit 120, the control system 220 can probe a heater wire adapter. When the expiratory conduit 120 is present in the respiratory assistance system 100, a heater wire adapter may be plugged into the humidification apparatus 104. In some embodiments, the heater wire adapter for the expiratory conduit 120 is added on to heater wire for the inspiratory conduit 106. The additional power drawn by the expiratory heater wire can be used to detect whether the heater wire is connected to the humidification apparatus 104. The expiratory heater wire, however, may not be connected when the expiratory conduit 120 is not present. Accordingly, the control system 220 can probe or interrogate the heater wire adapter to determine a resistance across the wire or the heater element. Probing may require sending a predetermined voltage across the wire.

In addition to detecting the absence or presence of the expiratory conduit 120, the control system 220 can also determine different types of tubes or conduits used in the respiratory assistance system 100 based on the value of the electrical resistance detected when the conduits are attached. The control system 220 can compare the detected value of electrical resistance with predetermined heater wire resistance values. The expiratory heater wire may also include a specific ID resistor, which can be used by the control system 220 to determine an expiratory limb. For example, different tubes may be used depending on whether the patient is an adult or an infant. In an embodiment, the control system 220 determines heater wire resistance in the conduits to determine the type of tube that is connected. Accordingly, based on the resistance values, the control system 220 can identify whether the respiratory assistance system 100 is connected to an adult or an infant patient. Further, if no resistance value is detected, the control system 220 can deduce that either the expiratory conduit 120 is not connected or the expiratory conduit 120 includes a water trap. In some instances, no current detection may also be a result of an error in connection. The control system 220 can store in the memory 924 the detected resistance value and the corresponding determinations.

As discussed above, the respiratory assistance system 100 can include multiple sensors. In some embodiments, the control system 220 can process data from these sensors to determine input conditions. For example, the control system 220 can process a humidity sensor input 204, a temperature sensor input 206, and a flow rate sensor input 208. The control system 220 can also process pressure sensor input instead of or in addition to the flow rate sensor input 208.

In some embodiments, the gas source 102 can include a humidity sensor to measure the relative humidity of the supply gas. The control system 220 can receive the input from the humidity sensor and change the system parameters, such as temperature set point depending on the measured humidity.

The control system 220 can also receive temperature measurements from the temperature sensors discussed above. Ambient air may have a different temperature than dry gases and generally tend to be warmer than dry gases. The temperature can be measured at the chamber inlet 111 or at any position that will give an indication of the temperature of the gas before it enters the humidification apparatus 104. The control system 220 can receive the temperature readings 206 and use the measurements in part to determine the gas source. In some embodiments, the temperature readings 206 may not be as useful for determining the gas source because some types of the gas source 102 may warm up gases prior to delivery to the patient. Further, the ambient temperature conditions may also vary. Accordingly, ambient temperature can also be measured and used by the control system 220 to validate temperature readings. Furthermore, the control system 220 can compare internal temperatures readings from the temperature sensors located at various locations in the respiratory assistance system 100 to determine the humidity condition of the supply gas.

In some embodiments, the control system 220 can assign weights to the measurements based on a confidence level corresponding with a particular measurement. The weights may be predetermined. The control system 220 can also compare measurements from independent sources (such as two different sensors) to determine inconsistencies. For example, the control system 220 can compare temperature measurements from temperature sensors located near the patient end, the chamber outlet 112, and the chamber inlet 111. The difference in detected temperature between these sensors can be used to identify the supply gas.

The control system 220 can also detect rebreathing and based on the detection, determine the type of therapy and gases source. In some instances, the exhaled gases from the patient may flow back through the inspiratory conduit 106. The exhaled flow may reach as far back as the chamber inlet 111. This flow pattern of exhaled air reaching as far back as the chamber inlet 111 may be more prevalent in a single limbed system. The control system 220 can thus use the exhaled gas or rebreathing detection to determine the type of gases source. A room air entraining ventilator is most likely used in a single limbed system. Thus, with the gases source identification, the control system 220 can also determine a particular configuration. For example, the control system 220 can measure parameters from the one or more inlet sensors. The control system 220 can determine temperature changes from a temperature sensor at the chamber inlet 111. When re-breathed gases travel through the conduit 106 and back through the chamber to the chamber inlet 111, the control system 220 can detect a higher temperature gas than the temperature of gases source. In an embodiment, the control system 220 detects a spike of temperature above a threshold for a threshold time. Based on this detection, the control system 220 can determine that there is exhalation flow reaching at or near the chamber inlet 111. Examples of rebreathing detection are discussed more in detail below.

The control system 220 can also analyse flow rate measurements from one or more flow rate sensors located in the respiratory assistance system 100. Based on the flow rate measurements, the control system 220 can detect flow directions of the gas. A detection of exhaled flow as discussed more in detail below can be used by the control system 220 to determine system conditions such as whether the respiratory assistance system 100 includes or does not include the expiratory conduit 120 or can be used to determine the type of gases source.

In some embodiments, the control system 220 can combine measurements from different types of sensors. For example, the control system 220 can monitor a combination of any one or more of a flow rate sensor, a humidity sensor, and a temperature sensor to determine the properties of supply gas. The flow rate sensor can provide a fast response and an indication of the direction of the flow. The humidity sensor can be located anywhere before the humidification chamber 134 and could be used by the control system 220 to fine tune the output, or could act as a switch, for example if the humidity level passes a certain threshold value. For a climate controlled room such as an ICU (Intensive Care Unit), relative humidity levels can be approximately 50% at about 21 degrees Celsius. This can correspond to about 8 mg/L to 16 mg/L absolute humidity depending on a sunny or a rainy day. In contrast, a compressed supply of gas or wall source may have a much lower humidity. Accordingly, in an embodiment, the control system 220 can set a threshold value of 8 mg/L or higher to differentiate between the two gases. The threshold value can also be 4 mg/L or higher or 1 mg/L or higher depending on the system configurations.

In some embodiments, the control system 220 can automatically determine the humidity of the input gas and change the set point for the humidification apparatus 104. As discussed above, entrained room air may have higher humidity than dry gases. Accordingly, the control system 220 may need to decrease the set point when entrained air or any air with higher humidity is used in the respiratory assistance system 100. The ambient air already contains humidity and is more likely to achieve saturation at the lower set point. For example, in an ICU environment, the temperature and relative humidity conditions are about 21 degrees Celsius and 50% respectively. But, the relative humidity level can vary by geography. It can be as high as 90% on a rainy day in Singapore. In contrast, for a dry gas supply, the control system 220 may maintain the set point to add as much humidity to the gas as possible given limitations imposed by the surface area of the evaporative surface. This is particularly advantageous with higher temperature ambient and/or incoming gas. While specific changes to the set point value are discussed herein (for example, increase, maintain, or decrease) for clarity, the set point is relative and can be changed by the control system, 220 to adjust humidity.

The control system 220 can also control the set point based on the type of therapy. For example, for invasive ventilation therapy, the respiratory assistance system 100 is most likely to include dry gas, for example, from a non-entraining gas source. For bubble CPAP or non-invasive ventilation therapy, the control system 220 may not need to adjust the set point depending on whether a dry gas supply or ambient air is used. Further, for high flow therapy, the control system 220 may need to change the set point depending on the type of supply gas. In some embodiments, if the control system 220 does not adjust the set point based on the different supply gas, the respiratory assistance system 100 may not be able to provide effective therapeutic care. For example, the respiratory assistance system 100 may have a higher level of condensate or a lower than desired level of humidification without set point compensation. The set point may be predetermined and stored in the memory 924. Thus, in some embodiments, the control system 220 changes set point based on the gases source detected and the type of therapy. As discussed above, set point is relative and can be increased, maintained, or reduced according to the predetermined values. In one embodiment, the set point is reduced when room entrained ventilator is detected and maintained when non room entrained ventilator is detected.

In some embodiments, the control system 220 can automatically determine the therapy based on determination of breathing patterns and flow. For example, the control system 220 can calculate a flow rate of 100 sLPM, which is most likely to be used in non-invasive ventilation therapy. The control system 220 can also determine leaks from vent holes or patient leak, or possible balloons. Non-invasive ventilation therapy is more likely to have higher magnitude of leaks. Accordingly, the control system 220 can measure leaks and determine that a non-invasive ventilation therapy is being delivered.

In some embodiments, the control system 220 can generate user interface screens to display on the user interface 140 in order to receive inputs from users. The inputs received can be used by the control system 220 independently from or in combination with the sensor measurements to determine system parameters. The control system 220 can also validate user inputs with the parameters calculated from the sensors as discussed above. If there is a mismatch in the user input and the calculated parameters, the control system 220 can generate an alert. The alert can be audio or visual or a combination. The control system 220 can also generate user interface screens dynamically based on the calculated parameters. The generated user interface screens can include suggestions generated by the control system 220 for the user to select via active links included in the user interface screens. In embodiments where the user interface 140 is a touchscreen, a user may interact with the user interface screens using touch. A user may also interact with the user interface screens through other means of data input. Thus, for example, user errors or automated configuration errors can be reduced or eliminated preventing potential harm to a patient.

Figure 3:
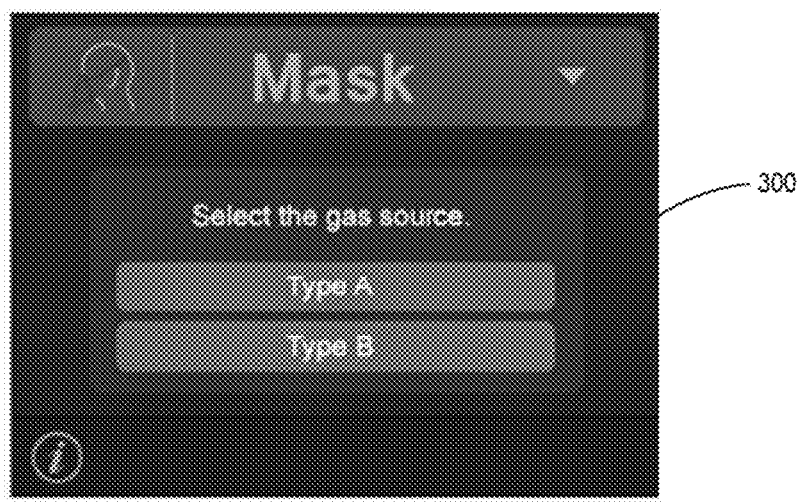
FIGS. 3-5 illustrate example user interface screens for receiving user input and providing status according to an embodiment of the present disclosure where the control system prompts a user to select a gas source type.
Figure 4:
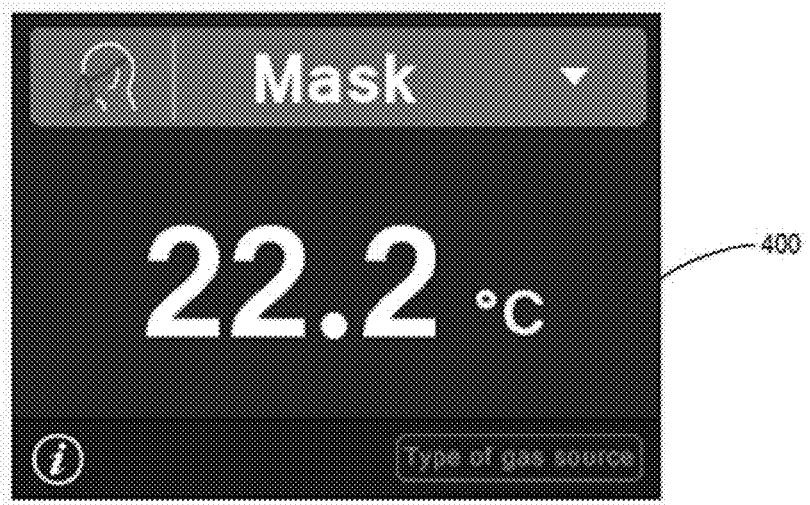
Figure 5:

FIG. 3 illustrates an embodiment of a user interface screen 300 generated by the control system 220. The user interface screen 300 can include an option for a user to select a particular gas source. For example, gas source type A can be an ambient air entrained gases source, and gas source type B can be a non-ambient air entrained gases source. After selection, the control system 220 can generate another user interface screen 400 as illustrated in FIG. 4. The control system 220 can automatically change the set point based on the user selection. The user interface screen 400 can indicate the set point temperature and the selected type of gas source. The control system 220 can further verify the user selection at steady state as shown in the user interface screen 500 illustrated in FIG. 5. The control system 220 can alert the user that the selection does not seem to conform with the calculated system parameters. Further, the control system 220 can present an option to the user to reject or confirm its automated detection.

Figure 6:
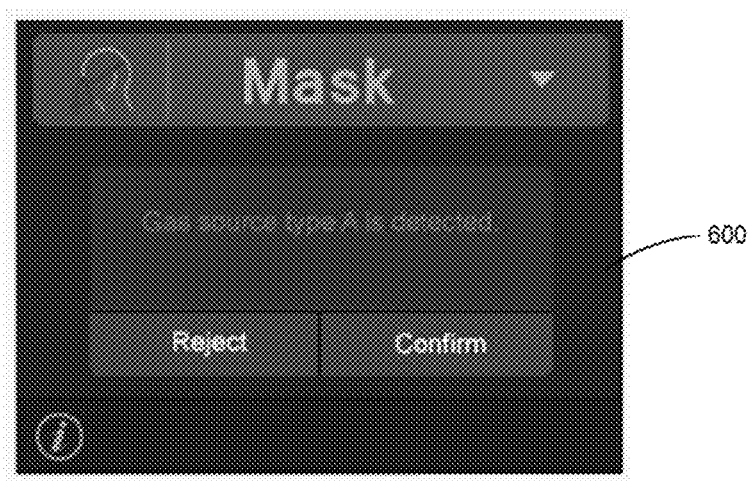
FIGS. 6-8 illustrate example user interface screens for receiving user input and providing status according to an embodiment of the present disclosure where the control system automatically determines a gas source type.
Figure 7:
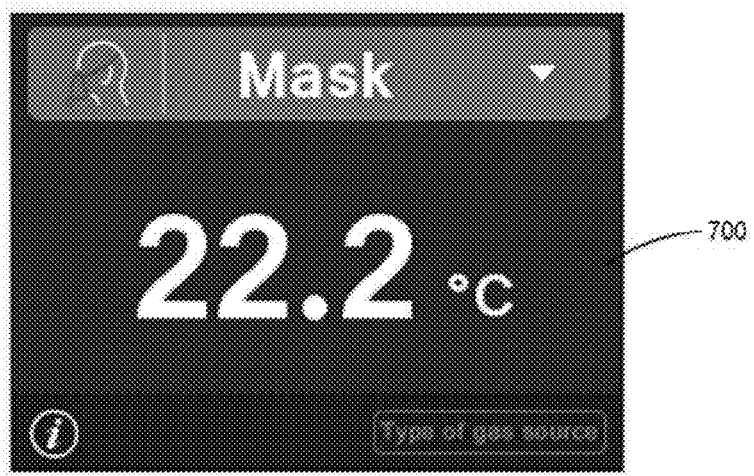
Figure 8:

FIG. 6 illustrates an embodiment of a user interface screen 600 generated by the control system 220. In this illustrated embodiment, the control system 220 automatically identifies the gas source and presents it in the user interface screen 600. If the user accepts the selection, then the control system 220 generates a user interface screen 700 shown in FIG. 7. And if the user rejects the selection, then the control system 220 can generate a user interface screen 800 shown in FIG. 8. The user interface screen 700 includes the type of gas automatically generated by the control system 220 and selected by the user. In some embodiments, the control system 220 automatically determines the gas source without user input. The control system 220 can show the gas source detected as illustrated in the user interface screen 700 or hide the detection as shown in the user interface screen 800. The control system 220 may automatically determine the gas source without user input in some embodiments when its measured confidence values are higher than a threshold. For example, if all the calculated parameters indicate a particular gas source, the control system 220 may not require user input.

In some embodiments, the control system 220 can start with a predetermined set point before the gas source is determined. The predetermined set point may vary for different types of therapies. The safety mode can occur after the warm up and before confirmation of the gas source.

Figure 10A:
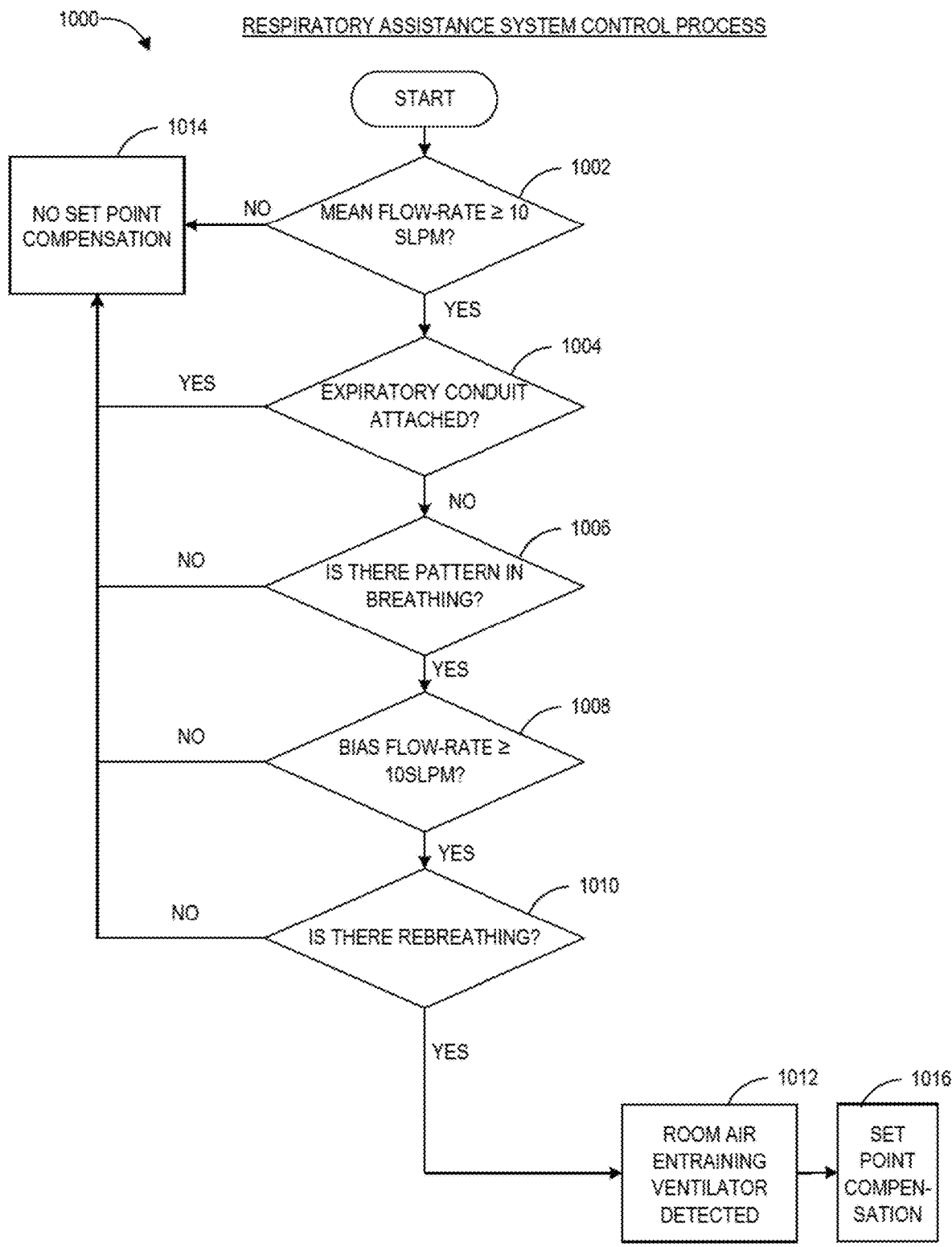
FIG. 10A illustrates a flow chart of a method for respiratory assistance system control according to an embodiment of the present disclosure.

FIG. 10A illustrates an embodiment of a process 1000 for determining the source of gas and accordingly managing the set point to control the estimated humidity condition of the respiratory gases provided to the patient. The process 1000 can determine whether no set point compensation is required as shown in block 1014 or set point compensation is required as shown in block 1016. The process 1000 can be implemented by any of the systems described herein. In some embodiments, the process 1000 is implemented by the control system 220 using the hardware processor 922. As discussed above, the control system 220 can use a combination of mechanical detection and sensor measurements. The control system 220 can get to a determination of whether a set point compensation is required at block 1016 using the sequential path illustrated in FIG. 10A. In an embodiment, set point compensation refers to changing the temperature set point parameter. Whether the temperature set point is increased or decreased can depend on the stored temperature set point. The control system 220 adjusts the stored temperature set point to maintain desired level of humidity.

In some embodiments, set point compensation can advantageously adapt for the humidity present in the gas before reaching the humidification chamber 134. As discussed above, for room air or ambient air entrained systems, the humidity can vary substantially. Accordingly, in some instances, if additional humidity was added without adaptation, it could cause condensation, patient discomfort, or other equipment malfunction. Thus, the control system 220 can use set point compensation to adapt for varying humidity levels in incoming gases. In an embodiment, the control system 220 adjusts the temperature or power supplied associated with the chamber heater 136 to change the amount of additional humidity added to the gases. In some embodiments, the control system 220 can also adjust the heater wire element(s) in combination with the chamber heater set point of one or more conduits based on a determination that set point compensation is needed. The determination of set point compensation can be based on a feedback loop. The control system 220 can determine the temperature at one or more locations in the respiratory assistance system 100 depending on the location of available sensors for measurement of temperature. The control system 220 can determine temperature from a sensor at chamber outlet 112 or at the patient end. In an embodiment, the control system 220 can use a combination of both or a weighted average.

In some embodiments, the process for determining the type of source gases 1000 begins at block 1002 with the control system 220 determining a mean flow rate of the gas and sequentially follows the process steps 1004, 1006, 1008, and 1010 to determine whether an air entraining ventilator is detected (block 1012). Determining the mean flow rate before performing other checks described in FIG. 10A can be advantageous to avoid processor intensive calculations. The control system 220 can determine the mean flow rate by calculating an average of the raw flow rate measurements provided by the flow sensor. In an embodiment, the control system 220 can use the mean flow rate for a quick initial validation that is less processor intensive than other checks. The mean flow rate can be used by the control system 220 to determine type of therapy being provided using the respiratory assistance system 100. In some embodiments, a lower mean flow rate might indicate the presence of the expiratory conduit 120 and likely usage of dry air. In this case no set point compensation might be required. In some embodiments, a lower mean flow rate might indicate that neonatal therapy is being provided. If the mean flow rate is higher than a threshold, the control system 220 may conduct further checks or determine that set point compensation is needed. In some embodiments, the threshold may be 10 sLPM; in other words, the threshold may be 10 sLPM at the reference temperature and pressure for which the flow sensor has been calibrated.

Additionally, at block 1004, the control system 220 may also detect a signal characteristic from an expiratory heater wire as discussed above and determine whether the respiratory assistance system 100 includes the expiratory conduit 120. The signal characteristic may correspond to the voltage or resistance measured from the heater wire. In some embodiments, if the control system 220 detects no signal, or noise possibly corresponding to an open circuit, the control system 220 can determine that it is likely that the respiratory assistance system 100 does not have the expiratory conduit 120 attached. In some embodiments, the control system 220 may deactivate set point compensation based on detection of the expiratory conduit 120. If the expiratory conduit 120 is not detected, the control system 220 can perform additional checks.

In some embodiments, the control system 220 can also detect breathing patterns as illustrated in block 1006. In some embodiments, breathing patterns relate to respiration rate. The respiration rate can be calculated by the control system 220 based on monitoring flow movements or pressure changes. The control system 220 can use the breathing patterns to determine the type of therapy. The control system 220 can determine that there is a pattern in the breathing by comparing the measured respiration rate with threshold values. For example, if the respiration rate falls within an acceptable range of respiration rates (6 to 60 breaths per minute) or if the calculated respiration rate between successive measurements is within 20% of the acceptable range of respiration rates, the control system 220 can determine that there is some pattern in breathing detected. Detection of this pattern may indicate the absence of the expiratory conduit 120 and that set point compensation is required.

Further, in some embodiments, the control system 220 can also determine a bias flow rate as illustrated in block 1008. The bias flow rate can represent the DC component of the flow rate of gases. The control system 220 can calculate the bias flow rate from raw flow rate measurements provided by the one or more flow sensors. In some embodiments, the flow sensor discussed herein includes a thermistor or a heated flow bead. For example, based on how much power is required to maintain a thermistor at a particular temperature, the control system 220 can determine a flow rate. Thus, a thermistor can be used as both a temperature sensor and a flow sensor. It may be advantageous in some embodiments to use one sensor, such as a thermistor, for measuring both flow rate and temperature. For example, at chamber inlet 111, adding another probe for a sensor may be cost prohibitive and may lead to a bulkier or inefficient design with complicated circuitry. Depending on the measurements needed, the control system 220 can activate different features of a sensor to extract either the flow rate or the temperature at a particular location. In some embodiments, the control system 220 can use the relationship between the bias flow rate and the mean flow rate to determine system configuration. The bias flow rate can be determined by the control system 220 based at least in part on a gradient or derivative of the raw flow rate signal as discussed more in detail with respect to FIG. 10B.

Figure 10B:
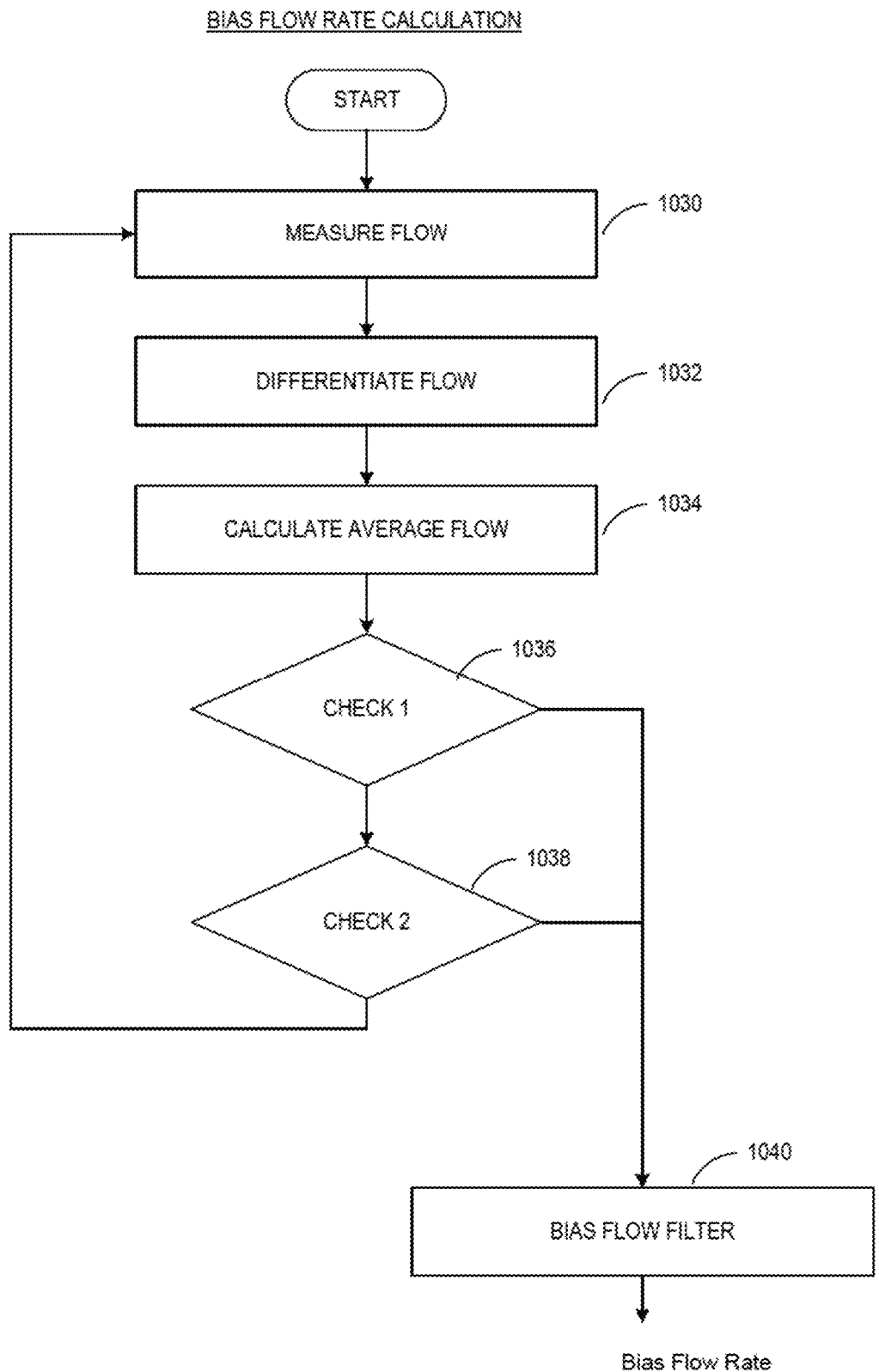
FIG. 10B illustrates a flow chart of a method for determining a bias flow rate according to an embodiment of the present disclosure.

FIG. 10B illustrates a block diagram of a process for determining bias flow rate. As discussed above, the bias flow rate can be determined from the raw flow rate. Accordingly, at block 1030, the control system 220 can determine the raw flow rate from one or more flow sensors. The flow sensors may be at the chamber inlet 111 and/or the chamber outlet 112 as discussed above. The data can be collected at a frequency of 10 Hz. The frequency can vary based on the type of sensor and the sampling rate for the sensor. In some embodiments, the frequency is greater than 1 Hz. In yet other embodiments, the frequency is less than or equal to 1 Hz. The control system 220 can then determine the rate of change of the measured flow rate at block 1032. In an embodiment, the control system 220 can use differentiation or other mathematical functions to determine the rate of change. The control system 220 can also calculate the average flow rate from the measured values of flow rates. The average flow rate can be a continuous average of flow rates. The average flow rate can also be an average from a limited time period. At block 1036, the control system 220 can perform a first check to determine if the measured flow corresponds to the bias flow. The control system 220 can check if the differentiated flow or rate of change is close to 0 and if the flow is less than the average flow. In some embodiments, the first check of rate of change close to 0 is to avoid maxima or minima of the flow signals. In an embodiment, the control system 220 determines that the rate of change of flow is within a range of plus or minus 1 sLPM per unit time. In some embodiments, the range can be greater than 1 sLPM per unit time or less than 1 sLPM per unit time. The value of 1 sLPM can be predetermined and stored in the memory. As discussed herein, the value can change based on geometry and other parameters of the respiratory assistance system 100. If the condition is satisfied, the control system 220 can store the measured flow rate at block 1040. The control system 220 can filter the stored values. The filter can include a smoothing filter. When determining bias flow, the control system 220 analyses points near the DC offset.

In some embodiments, the control system 220 is determining that the flow rate measurement is not changing substantially or that the flow rate signal is stable, indicating a constant breathing pattern. In this case, the bias flow is substantially equal to the gases flow rate. Accordingly, the mathematical operations discussed herein are used by the control system 220 to extract the bias flow rate.

In some instances, the flow measurements may be affected by noise or changing too fast. For example, when a patient is hyperventilating or in younger patients, the control system 220 may not be able to identify from the first check whether the measured flow represents bias flow because of the high breathing rates. For example, the control system 220 might miss when the rate of change is at 0. Accordingly, in some embodiments, the control system 220 can perform a second check at block 1038 to capture flow measurements that are close to the zero crossing point since the flow signal is a rapidly changing signal. The control system 220 can check if the flow rate signal is stationary. The control system 220 can determine if the differential flow rate or rate of change crossed the zero point when compared to the previous rate of change of flow calculation and if the flow rates are below the current average flow rate. If the condition is true, the control system 220 can store the flow rate as the bias flow rate at block 1040, which may subsequently be filtered as discussed above. The filtered bias flow rate can be used by the control system 220 to determine bias flow condition at block 1008 as discussed below with respect to FIG. 10A.

Figure 14:
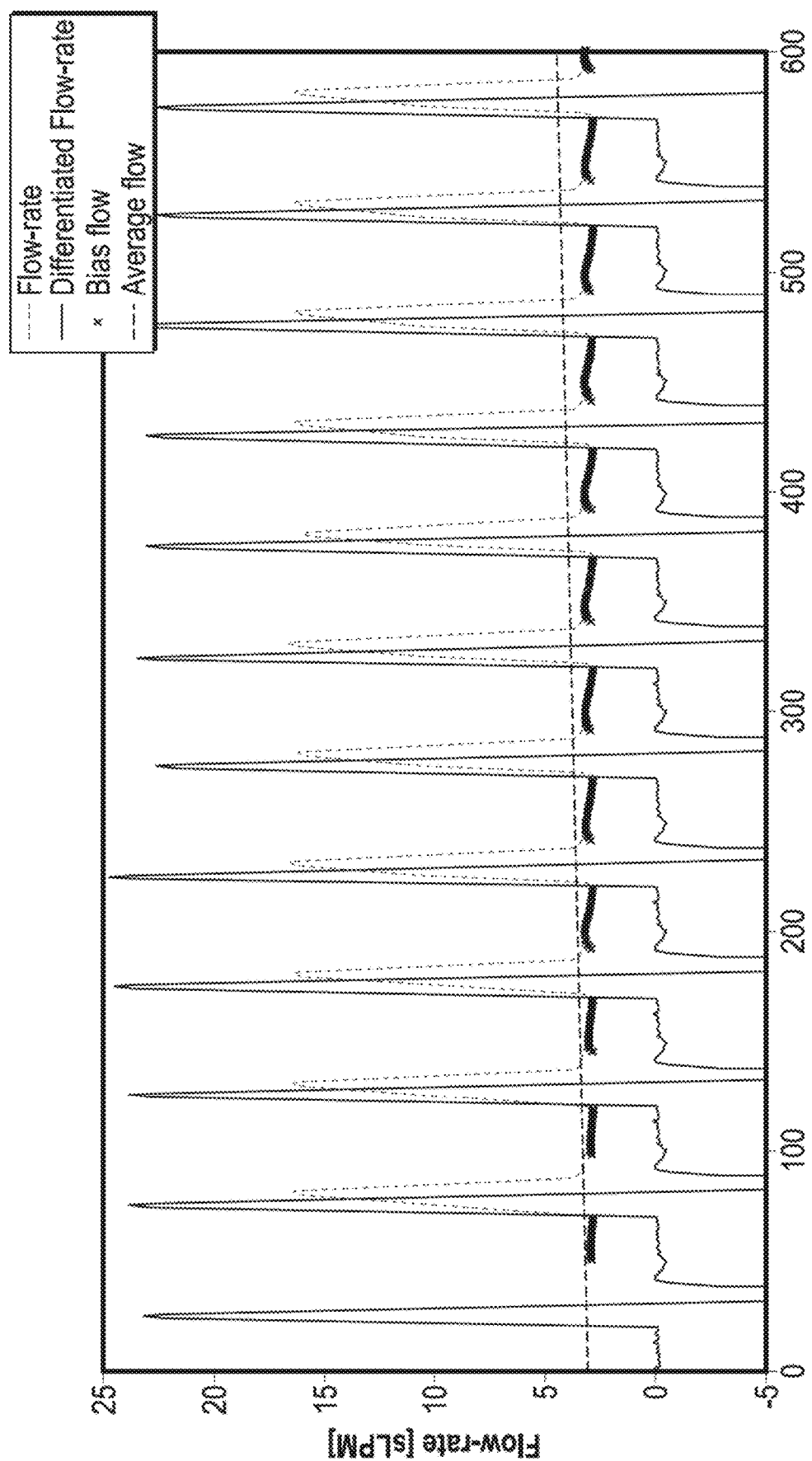
FIG. 14 illustrates an example plot of bias flow rate, rate of change of flow rate, raw flow rate, and the average flow rate according to an embodiment of the present disclosure.

The bias flow rate is likely to be higher for a room air entraining ventilator with no expiratory conduit 120. For a closed loop system using a non-entraining ventilator, the bias flow rate is likely to be lower. A bias flow rate above a threshold can indicate the absence of the expiratory conduit 120. In some embodiments, the threshold is 10 sLPM. In some embodiments, the threshold can be greater or less than 10 sLPM. The absence of the expiratory conduit 120 can indicate use of ambient air and that set point compensation is required. An example plot of bias flow rate, rate of change of flow rate (i.e. differentiated flow rate), raw flow rate, and the average flow rate is shown in FIG. 14. The flow rates described herein can be measured in litres per minute (LPM), standard litres per minute (sLPM), or as power dissipation. While references to specific flow rates discussed in this application are made in sLPM, the rates can be converted to other units. Also, the specific values, such as the example threshold value of 10 sLPM may change according to the structure or geometry of the components.

Figure 11A:
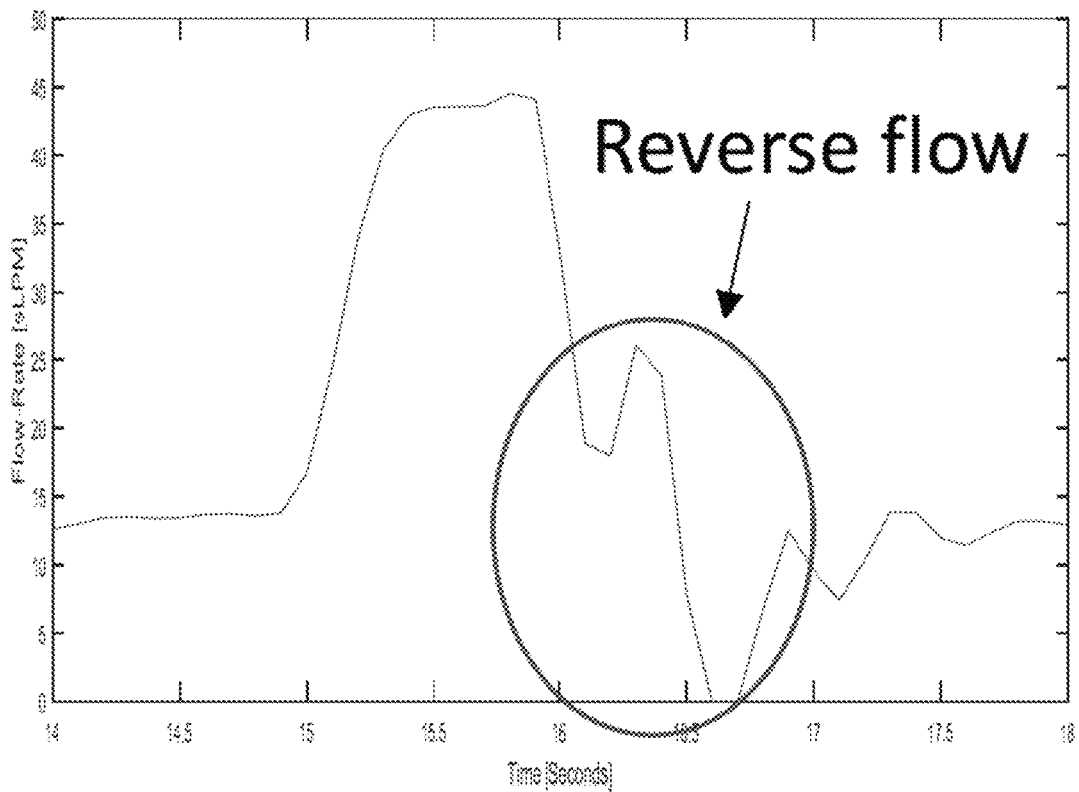
FIG. 11A illustrates a flow rate pattern shown in a graph of a flow rate versus time.

In some embodiments, the control system 220 calculates an adjusted mean flow rate, which can better correspond to the actual mean flow rate. The unadjusted average of the raw flow rate measurements provided by the flow sensor can underestimate the actual mean flow rate. This is the result of two conditions: 1) inspiratory breath has higher frequency components than the expired breath. For example, a normal adult has I/E ratio of 1/2 to 1/3. That is, if inspiration time takes 1 second, than expiration time is twice or three time as long; and 2) the flow sensor may be too slow to represent the actual breath pattern because it can act as a low-pass filter. Therefore, in some embodiments, the flow sensor (low-pass filter) filters out more of the inspired breath and less so of the expired breath. Accordingly, the raw mean flow-rate can be biased low and align towards the expired breath. The control system 220 can adjust the raw flow rate by reversing the effect of the low-pass filtering introduced by the flow sensor to reconstruct the original breath pattern. The adjusted mean flow-rate is the averaged flow-rate of the reconstructed breath pattern as shown in FIG. 11A.

Returning back to block 1010 of FIG. 10A, the control system 220 can detect flow rate patterns from monitoring flow rate and direction of the gas as discussed below and with respect to FIGS. 10C and 11A,B. The control system 220 can detect rebreathing patterns to determine the type of ventilator. FIG. 11B shows a diagram to illustrate flow detection. As gases move in and out of the chamber inlet 111 and chamber outlet 112, they are affected by the geometry or shape of the system. Based on gas law principles, the control system 220 can detect the flow profile and determine a rate of change between inspiratory and expiratory gases because, depending on the position of the sensor at inlet or outlet, the gases may be going from one geometric dimensions to a different geometric dimensions. The control system 220 can use the disparities in geometry and the corresponding changes to the flow rate to determine flow patterns as discussed more in detail below. While the illustrated flow patterns are for a particular shape, the control system 220 can operate on humidification chambers of different geometries and detect different flow patterns. For example, the control system 220 may store predetermined flow patterns for different geometries.

In an embodiment, for a single limb system, the flow sensors at the inlet and at the outlet are both turned on to enhance observed exhaled flow. As discussed above, it may be advantageous in some embodiments to include one sensor to measure flow and temperature. Accordingly, the control system 220 can selectively turn on particular sensors based on the required measurements. The timing can be a function of processor resources and system parameters. The magnitude change relative to each of the flow sensors is used to determine the direction of flow. This can be used to detect that a room air entraining ventilator is being used. Once the room air entraining ventilator has been detected, the control system 220 can adjust set point. In an embodiment, the inlet flow bead or inlet flow sensor is turned on for 3 minutes every 30 minutes for measurement purposes. The control system 220 can manage the operation of inlet flow bead across many frequencies and time intervals. The control system 220 can also operate the sensor at the chamber inlet 111 in a pulsed sequence so that the inlet sensor is switched between acting as a temperature sensor and a flow sensor. In some embodiments, there are separate temperature and flow sensors at the chamber inlet 111. Accordingly, the control system 220 may not need to operate these in sequence in such embodiments.

Figure 10C:
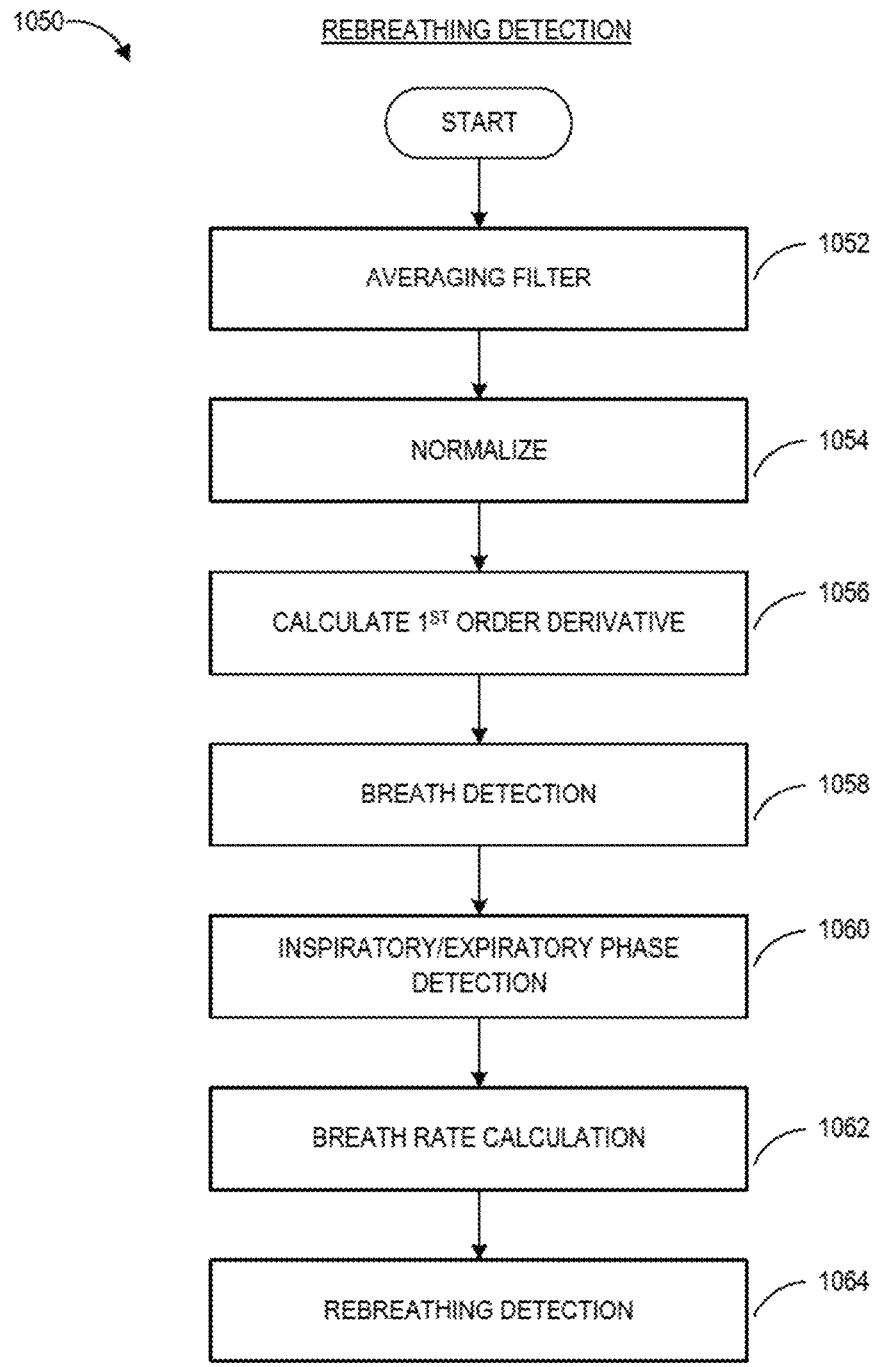
FIG. 10C illustrates a flow chart of a method for detecting rebreathing according to an embodiment of the present disclosure.
Figure 11B:
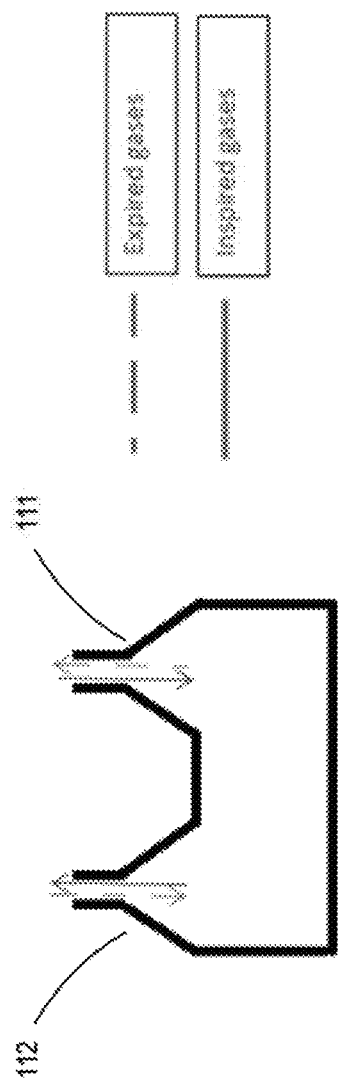
FIG. 11B illustrates a schematic model of an inlet and an outlet with direction of flow of air according to an embodiment of the present disclosure.
Figure 12A:
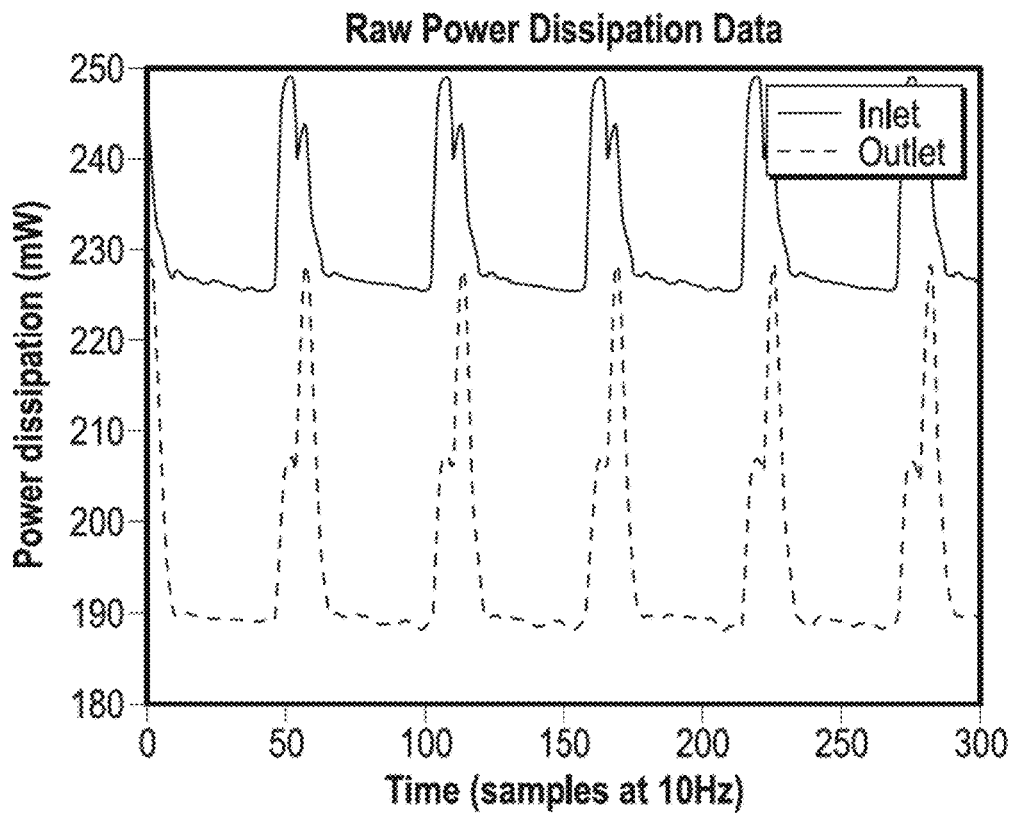
FIG. 12A illustrates example plots of measure raw power dissipation data for the inlet and the outlet in room air entraining ventilator according to an embodiment of the present disclosure.
Figure 12B:
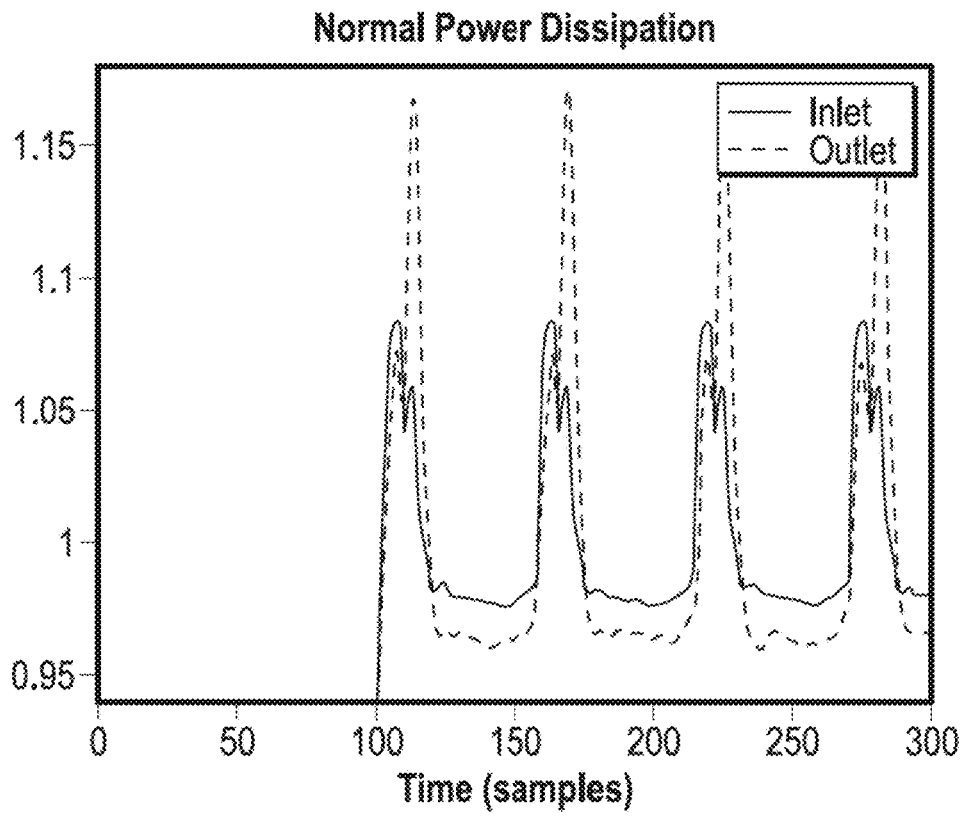
FIG. 12B illustrates a normalized power dissipation of the example plots shown in FIG. 12A.

FIG. 10C illustrates an embodiment of a process 1050 for rebreathing detection. The control system 220 can collect flow rate sensor measurements. In an embodiment, the sensors measurements are collected at a frequency of 10 Hz. As discussed above, the sampling frequency may vary depending on the sensor. The flow sensor measurements can be collected as power dissipation values, for example, in mW. While the illustrations specifically refer to flow rates measured through power dissipation, the control system 220 may use other units or processes to detect flow rates. At block 1052, the control system 220 can use an averaging filter to determine an average value of the flow measurements. In an embodiment, the control system 220 implements a 100 sample time constant IIR (Infinite Impulse Response) filter to determine the DC value of the measurements. Other sample times can also be used. For example, in some embodiments, the sample times can be 200, 300, more than 300, or less than 100. The control system 220 can apply the filter on both the inlet and outlet flow sensors to calculate respective inlet and outlet average power dissipation. An example plot representing power dissipation is shown in FIG. 12A for both the inlet and the outlet measurement sites. At block 1054, the control system 220 can normalize the inlet and outlet average flow rate values. Normalization can enable comparison of the power dissipation profile between the inlet and outlet. In an embodiment, the control system 220 waits a predetermined amount of time before normalization to stabilize the averaging filter. An example plot of normalized power dissipation is shown in FIG. 12B. In some embodiments, the power dissipation measurements can also be represented as flow rate.

Figure 12C:
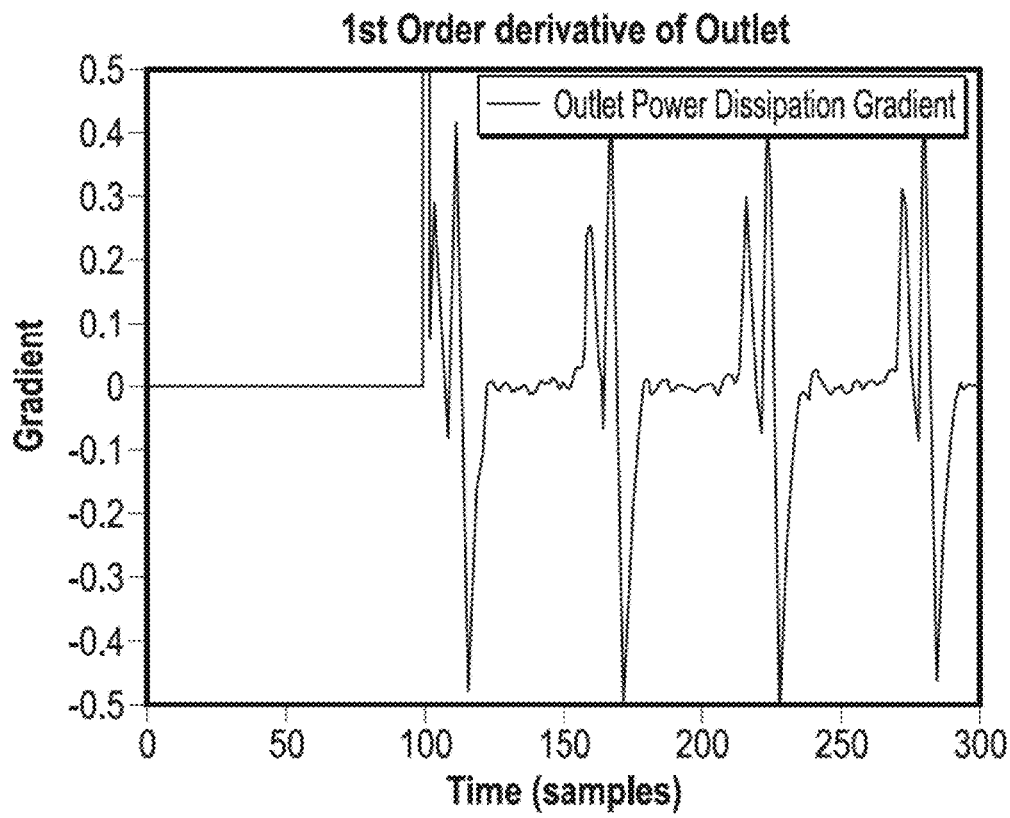
FIG. 12C illustrates a rate of change of the power dissipation plot of the outlet shown in FIG. 12A.

At block 1056, the control system 220 can calculate a gradient, a derivative, or a rate of change of the normalized power dissipation measurements with respect to time. An example plot of the gradient of the normalized power dissipation measurement is shown in FIG. 12C.

Figure 12D:
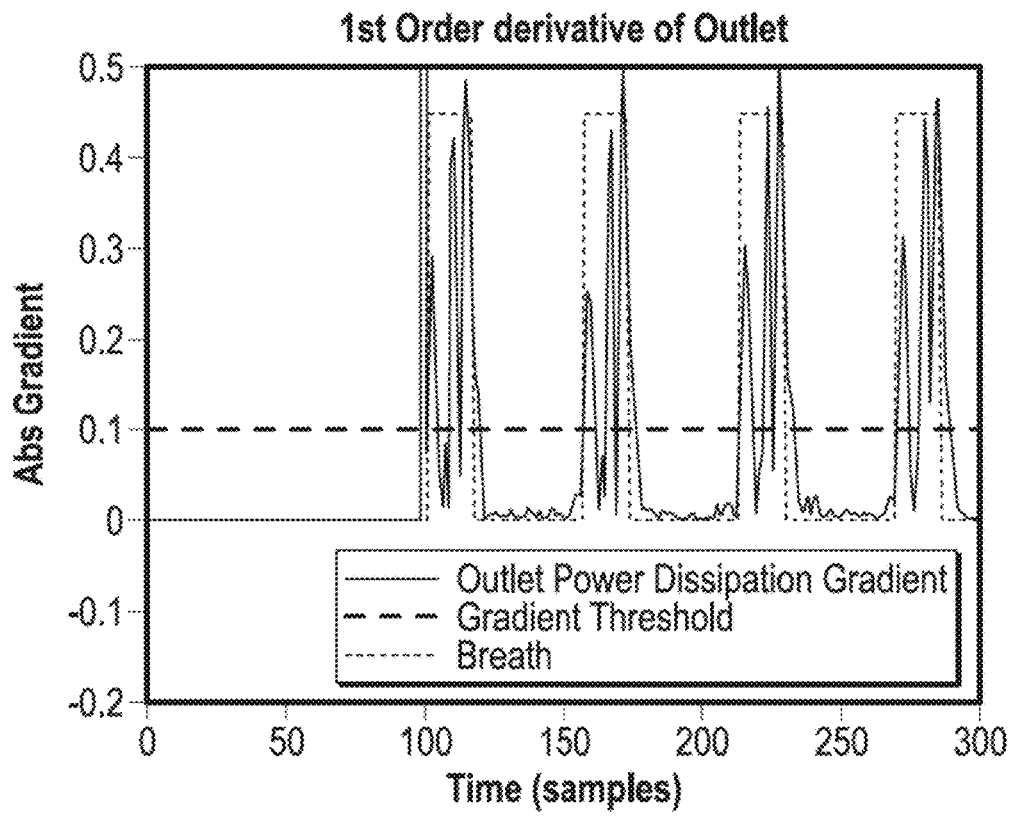
FIG. 12D illustrates an absolute rate of change of FIG. 12C with an example detection of breath and gradient threshold according to an embodiment of the present disclosure.

The control system 220 can detect breath of a patient based on the gradient calculation at block 1058. The control system 220 determines the absolute gradient of the outlet power dissipation. If the maximum of the past X number of samples exceeds a gradient threshold and the normalized power dissipation value exceeds a normalized power threshold, the control system 220 determines that the portion of the signal corresponds to a breath. The control system 220 can store the time of occurrence in the memory. In an embodiment, X is 10 samples per unit time, the gradient threshold is 0.1, and the normalized power threshold is 1.01. FIG. 12D illustrates an example plot of the outlet power gradient, the gradient threshold, and the detected breath. While the above description is with respect to the outlet flow sensor, the control system 220 can also determine breath based on a similar analysis on the inlet flow sensor.

The thresholds are selected to determine breath occurrences with reduced number of false positives. The gradient threshold (0.1 in the embodiment discussed above) applied on the rate of change can indicate that a breath may be present within a particular time window. Based on this detection, the control system 220 can perform a second check of determining whether the normalized power dissipation within the particular window is above a normalized power threshold (1.01 in the example above). The second check can mitigate for noise, which may result in false detection of breath. For example, there may be cross-over between the inlet and outlet signals. This could lead to this region being misclassified, but it may be a result of noise. To exclude noise, the control system 220 classifies regions only above the normalized power threshold in some embodiments. Accordingly, in the example embodiment discussed above, the control system 220 classified breath only for regions where the inlet or the outlet signal is greater than 1.01. If both are less than 1.01, this part of the signal is excluded in the example embodiment. Accordingly, the normalized power threshold can be set based on the noise floor or DC offset of the system. A higher duty cycle may likely lower this threshold, while a lower duty cycle is likely increase the threshold value.

Once a breath is detected and the noise excluded, the control system 220 can detect or differentiate between inspiratory and expiratory phase at block 1060. In an embodiment, the inlet and outlet signals are compared to determine if the difference between them is greater than a phase threshold. In an embodiment, the phase threshold is 0.017. When the difference between the signals exceeds the phase threshold, the control system 220 can determine whether it is in inspiration or expiration. When inlet signal is greater than the outlet signal by the phase threshold, the control system 220 can determine that it is inspiratory phase. Further, when the outlet signal is greater than the inlet signal by the phase threshold, the control system 220 can determine that it is expiratory phase. As discussed herein, the relationship between the duration or length of the phases can be used to determine if rebreathing is occurring. For example, if the length of the expiratory phase in time divided by the length of the inspiratory phase in time is greater than a rebreathing threshold, then it is likely an indication of rebreathing. In an embodiment, the rebreathing threshold is 0.3. As discussed above, the exact value for the thresholds discussed above may vary depending on system parameters. For example, different filters, sensors, sampling rate, geometry may change the thresholds. The function of the threshold values is to extract the relevant parameters while reducing instances of false positives.

In another embodiment, the control system 220 can also identify at block 1060 whether the detected breath corresponds to inspiration or expiration based on area under the curve. For example, the control system 220 can compare the power dissipation or flow rate profile measured at the inlet and outlet flow sensors. The control system 220 can determine that it is likely an expiratory portion of the breath if the normalized power dissipation profile from the outlet sensor is greater than the normalized power dissipation profile from the inlet sensor. The exhaled gases flow has a different flow rate to the gas flow of therapy gases when travelling across the outlet sensor based on the geometrical differences described herein. In an embodiment, the control system 220 can determine this from area under the curve or other similar comparison analysis. If it is determined that it is not likely to be an expiratory portion of the breath, the control system 220 can assign that portion to be inspiratory portion of the breath. Accordingly, the control system 220 can determine breaths and the inspiration and expiratory portions of the breath from the flow sensor measurements at two different portions of the humidification system.

Figure 12E:
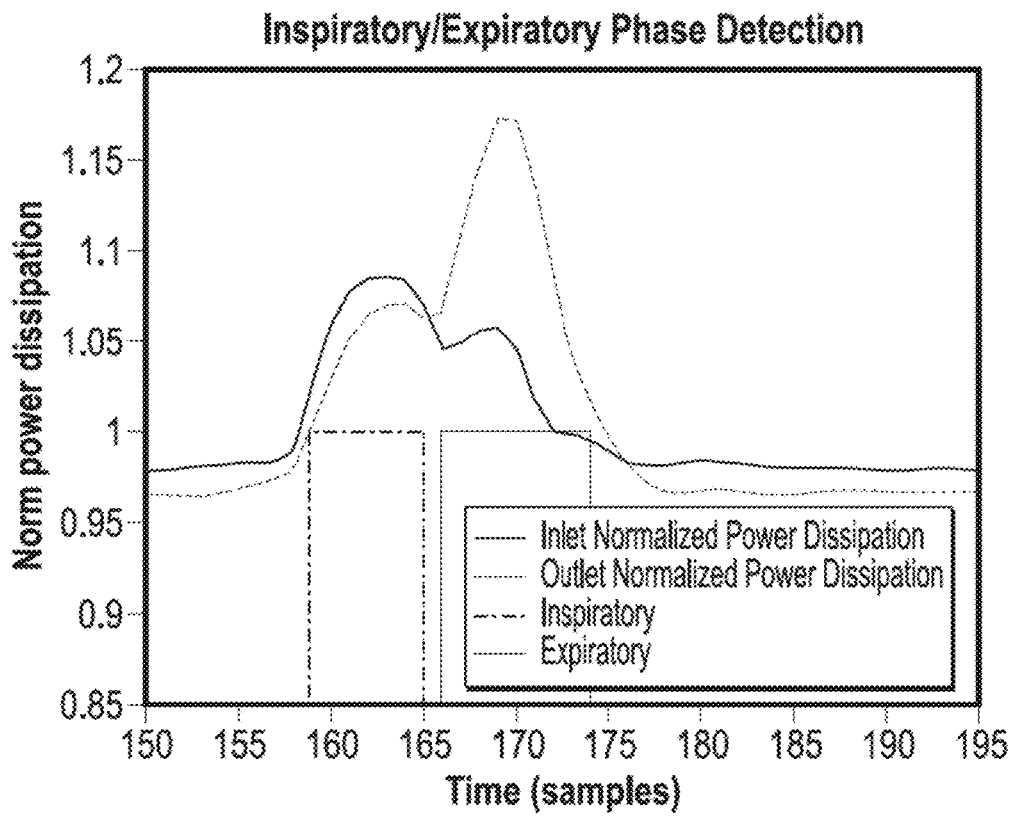
FIG. 12E illustrates an example detection of inspiratory and expiratory phase according to an embodiment of the present disclosure.
Figure 12F:
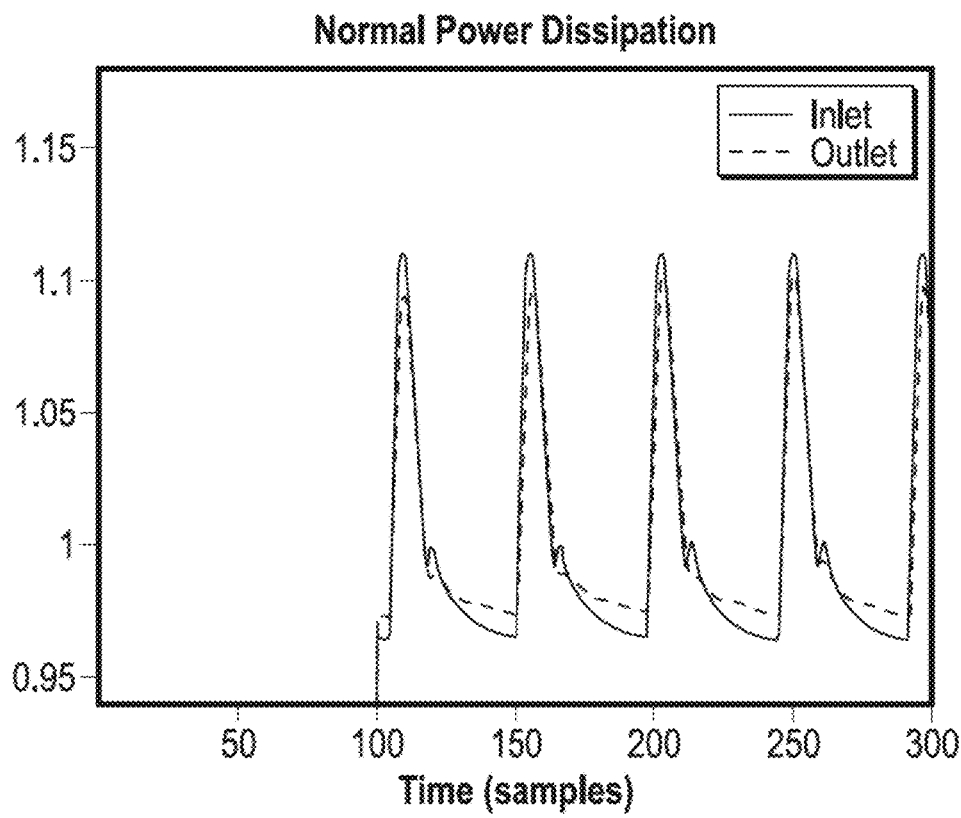
FIG. 12F illustrates an example of normalized power dissipation measurements from inlet and outlet sensors in a non-entraining ventilator according to an embodiment of the present disclosure.
Figure 12G:
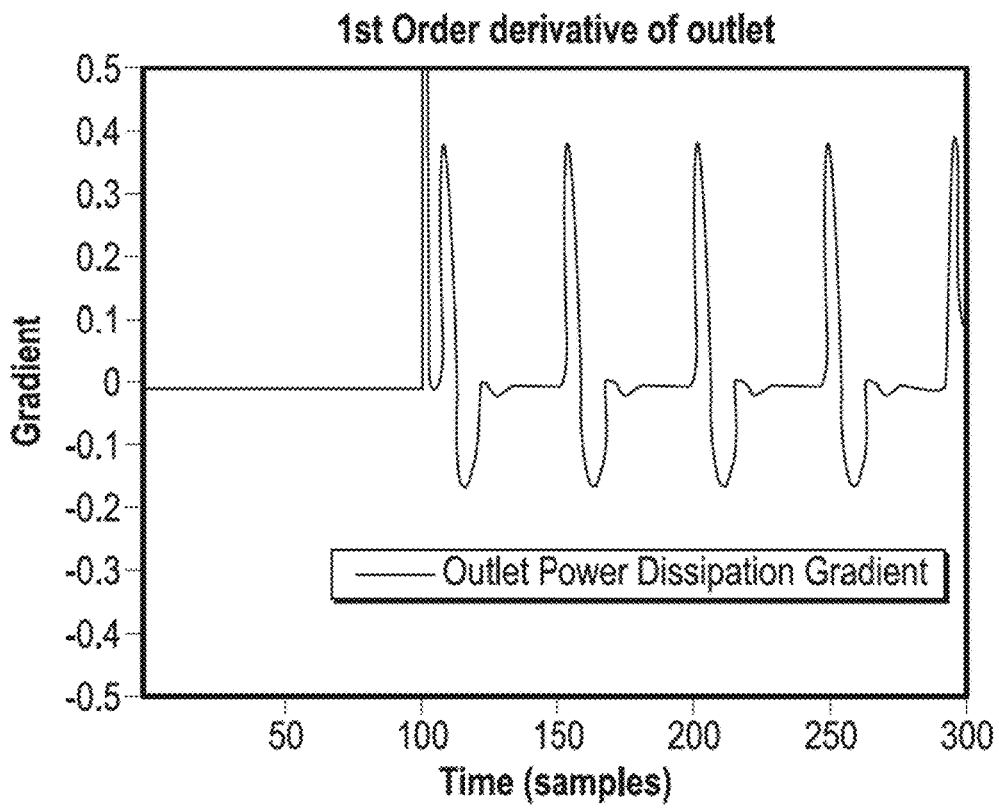
FIG. 12G illustrates a rate of change plot of the outlet power dissipation of FIG. 12F.
Figure 12H:
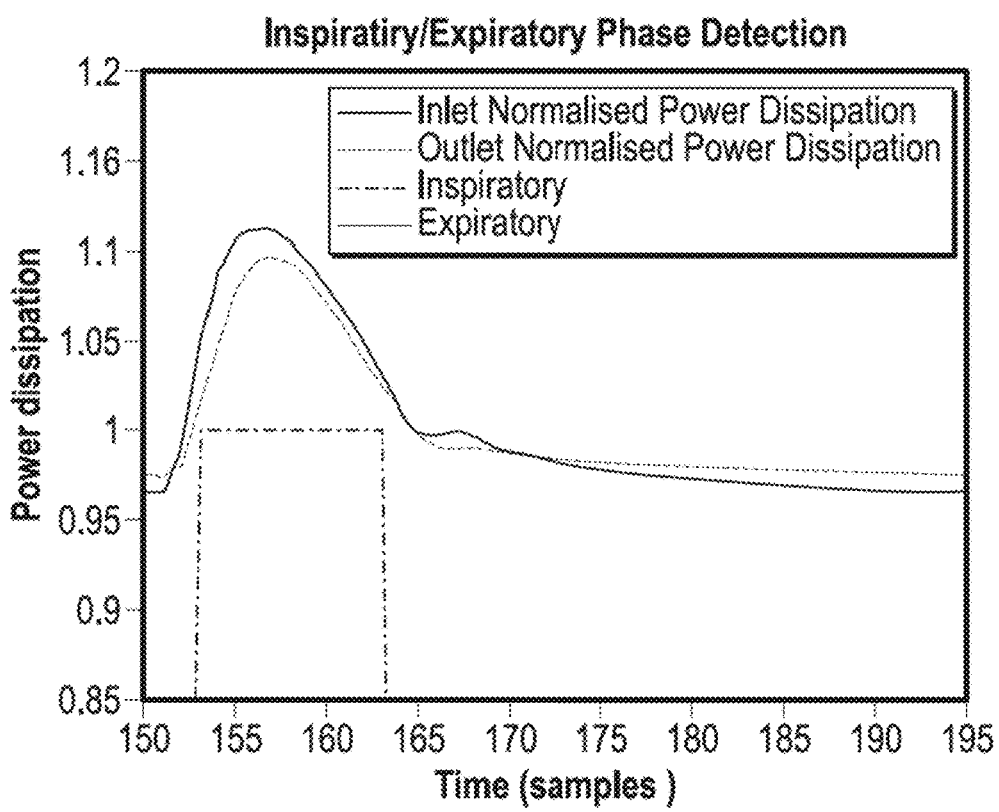
FIG. 12H illustrates an inspiratory and expiratory phase detection of the example plots of FIG. 12F according to an embodiment of the present disclosure.
Figure 12I:
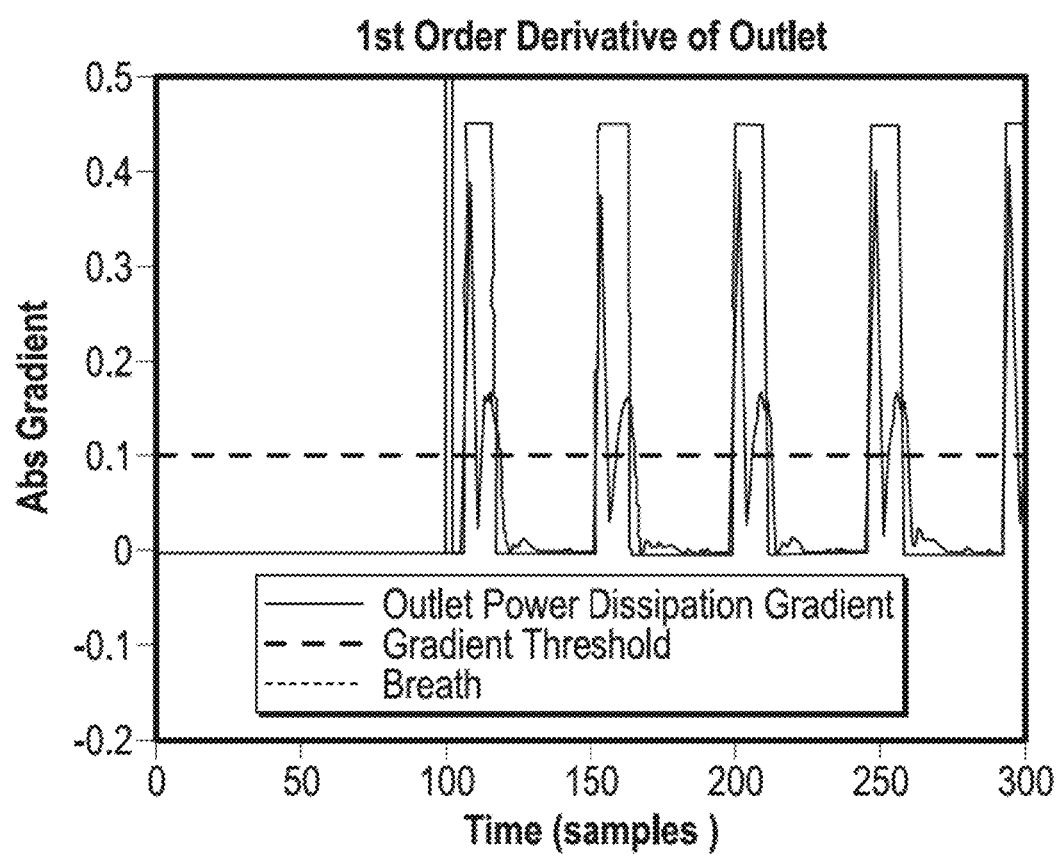
FIG. 12I illustrates a rate of change of the outlet power dissipation of FIG. 12F, an example gradient threshold, and an example breath detection according to an embodiment of the present disclosure.

In some embodiments, the control system 220 can optionally determine the breathing or respiration rate at block 1062 based on the detection of breath. An example plot of the comparison and detection of inspiration and expiration is shown in FIG. 12E. In an embodiment, the breathing rate relates to the periodicity of breath detection. The breathing rate can be used by the control system 220 to determine breathing patterns as discussed with respect to block 1006 in FIG. 10A. The breathing rate for the exhaled gases flow is different due to the mechanical configuration of the chamber. The speed at the inlet and outlet of the chamber is different during the expired flow as compared to inspired flow. The control system 220 can use these predetermined differences to determine mechanical configuration from the breath rate. The control system 220 can also output breath rate in some embodiments.

In some embodiments, the rebreathing detection at block 1064 can be determined by identifying double peaks. If the control system 220 determines that the flow pattern includes double peaks due to rebreathing, then it is likely that the gas source 102 may be a room air entraining ventilator. For example, in FIG. 11A, the threshold flow is about 13 sLPM. The gas source 102 being a room air entraining ventilator may further indicate use of ambient air and accordingly the control system 220 can determine that set point compensation is required. If set point compensation is required, the set point may be changed by the control system 220.

Figure 13A:
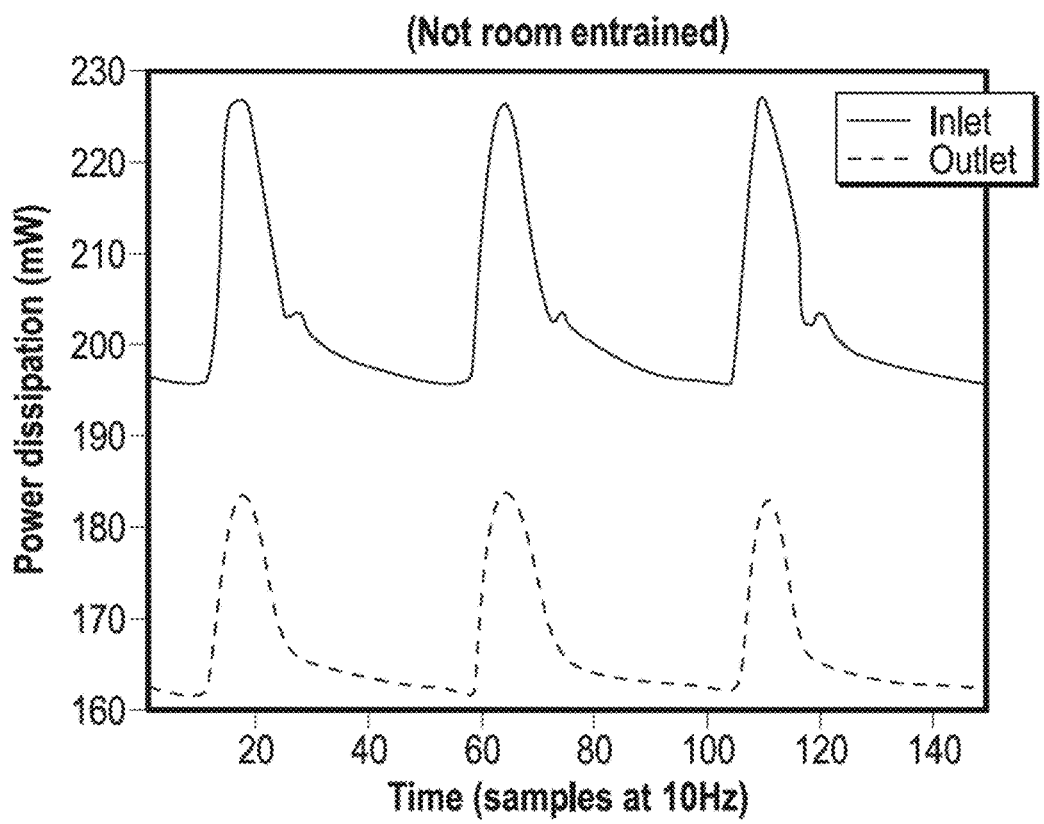
FIGS. 13A and 13B illustrate additional power dissipation profiles from the inlet flow sensor and the outlet flow sensor of a non-entrained ventilator according to an embodiment of the disclosure.
Figure 13B:
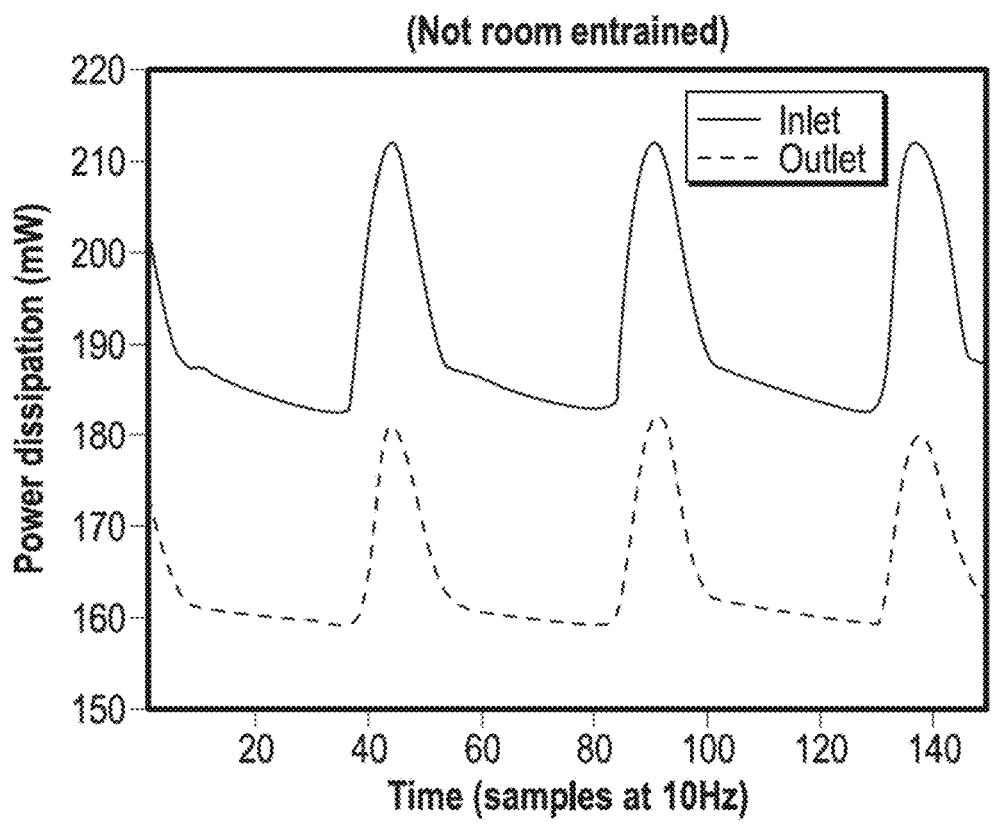

FIG. 13A to 13D illustrate power dissipation profiles from the inlet flow sensor and the outlet flow sensor of two different types of ventilation systems: FIGS. 13A and 13B (non-entrained) vs. FIGS. 13C and 13D (entrained). In some embodiments, the control system 220 can detect the patterns in the power dissipation profiles to determine rebreathing. For example, based on the power dissipation profile, the control system 220 can determine whether room entrained ventilators or non-room entrained ventilators are used. As can be seen in FIGS. 13A and 13B, there is no discernible double peak in the outlet power dissipation profile. Comparatively, FIGS. 13C and 13D clearly show a double peak 1302. The existence of a double peak can be used by the control system 220 to determine that room entrained air is used in the ventilation system.

Figure 13C:
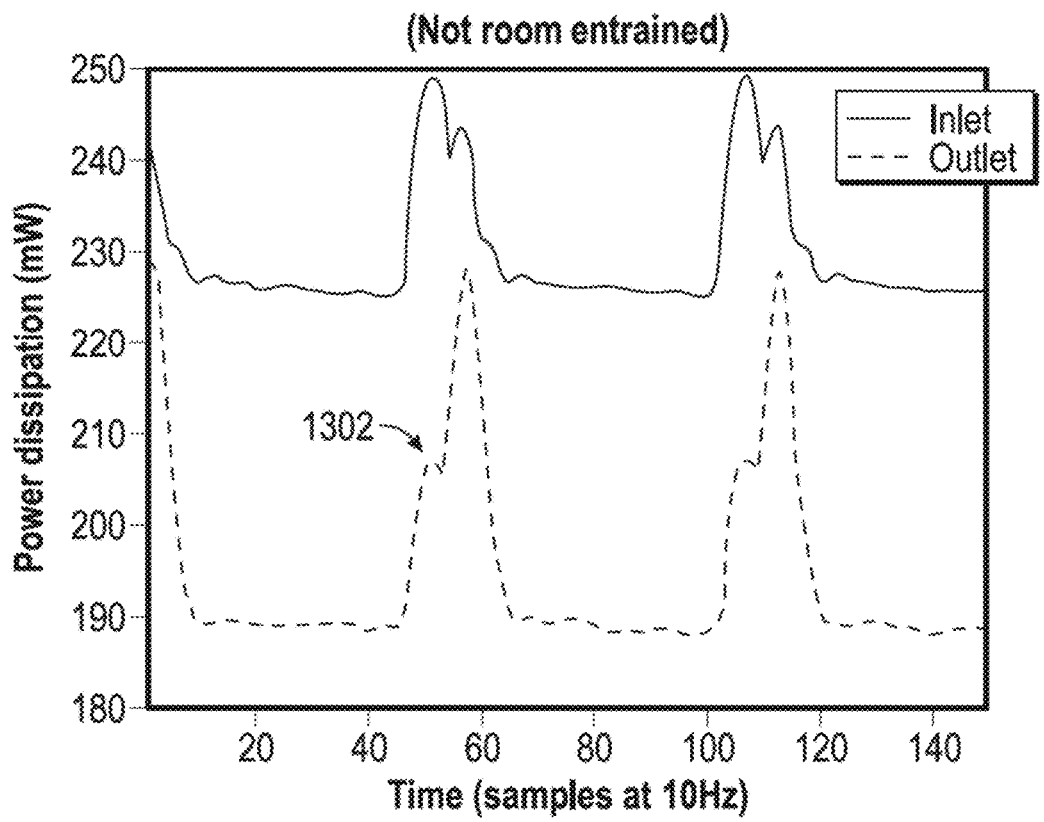
FIGS. 13C and 13D illustrate additional power dissipation profiles from the inlet flow sensor and the outlet flow sensor of a room air entrained ventilator according to an embodiment of the present disclosure.
Figure 13D:
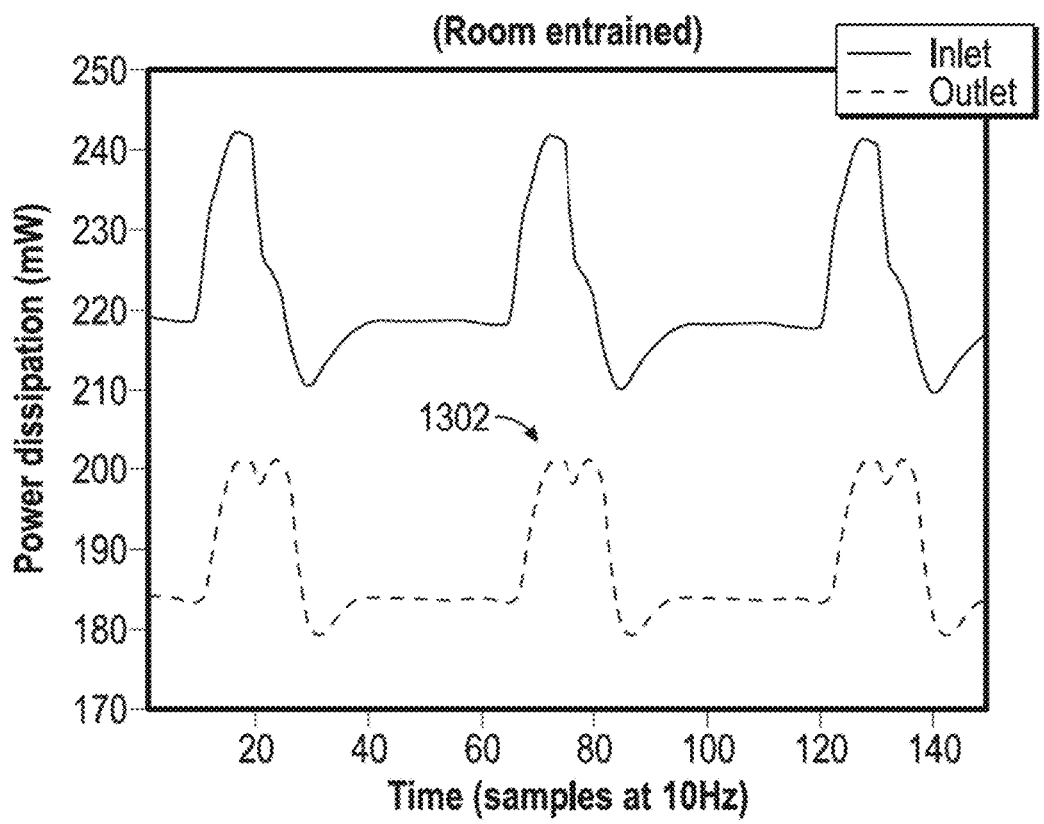

In some embodiments, instead of comparing power dissipation profiles, the control system 220 can cross correlate the inlet power dissipation and outlet power dissipation curves to detect rebreathing at block 1064. For example, the control system 220 can execute averaging filter and normalization as discussed above with respect to blocks 1052 and 1054. Then, instead of executing the steps 1056 to 1062, the control system 220 can detect rebreathing as discussed below. Referring to FIGS. 13A and 13B, the inlet power curve and outlet power curve are substantially aligned. The peaks align because gases are only going one way i.e. toward the patient because it is a dual limb system. In general, non room entrained vents are associated with a dual limb arrangement. FIGS. 13C and 13D show the dissipation curves for a room entrained vent (that generally is associated with a single limb). The peaks of the outlet do not align with the peaks of the inlet. This is because of rebreathing, the exhaled flow being detected at the sensor near the outlet 112. The control system 220 can store a snap shot of several samples over time. The control system 220 can compare or use a cross correlation function across a number of samples shown for example in FIGS. 13A and 13B using a moving window. In some embodiments, the control system 220 can select a single period for cross-correlation. Based on this comparison or cross-correlation, the control system 220 can detect rebreathing. The control system 220 can use one or more of the multiple methods of rebreathing detection described above, individually or in combination.

Going back to FIG. 10A, if rebreathing is detected, the control system 220 can determine that a room air entraining ventilator is detected at block 1012 and accordingly set point compensation may be needed as shown in block 1016.

In some embodiments, the control system 220 does not need to determine rebreathing or the other steps shown in FIG. 10A and instead determine the type of gases source based on the temperature measurement at the chamber inlet 111. Accordingly, the following process can be used in conjunction with aspects of the process 1000 discussed with respect to FIG. 10A or separately to differentiate between room entraining ventilators or non-room entraining ventilators. For example, the control system 220 can store a predetermined temperature for ambient air in a hospital. In an embodiment, the predetermined temperature is 22 degrees Celsius. The control system 220 can also receive an input for the ambient temperature. If the temperature sensor at the chamber inlet 111 measures the temperature of incoming gases to be close to the predetermined temperature, the control system 220 can determine that this is a reasonable indication that the ventilator is entraining air and may require set point compensation. Wall gases are generally much lower in temperature, typically below 15 degrees Celsius. The control system 220 can determine if the temperature sensor at chamber inlet 111 detects a supply gases temperature of lower than 15 degrees and use that as indication of a non-room entrained air and no set point compensation. In another embodiment, the control system 220 can determine if the temperature of gases at the chamber inlet 111 is greater than or less than the ambient temperature. If it is greater, then the control system 220 can determine that to be a result of a room air entraining ventilator, and if lesser, then likely a non-entraining ventilator. Wall gases are typically substantially dry with minimal entrained moisture. In some embodiments, the control system 220 can use the above process of measuring air temperature at the inlet 111 instead of or in addition to the other processes described herein to provide a more accurate indication of whether the ventilator is a room air entraining ventilator or a non-entraining ventilator.

The set point may be applied to the heater plate temperature. In some embodiments, the set point may be applied to the temperature of the gas at the chamber outlet 112 or in the conduit or near the patient interface 116. The set point may also be applied to the current provided to the heater wires in the inspiratory conduit 106 or the expiratory conduit 120. FIG. 10 describes multiple method steps and measurements. However, the process 1000 is not limited to the steps illustrated. Other measurements described herein can also be included in determining operation of the respiratory assistance system 100. Further, some of the steps illustrated may be optional or not included based on specific configuration of components. For example, if the respiratory assistance system 100 is not capable of providing high flow therapy, some of the decision logic can be left out. Further, the lack of high flow capability may itself be used by the control system 220 to determine system conditions.

Figure 10D:
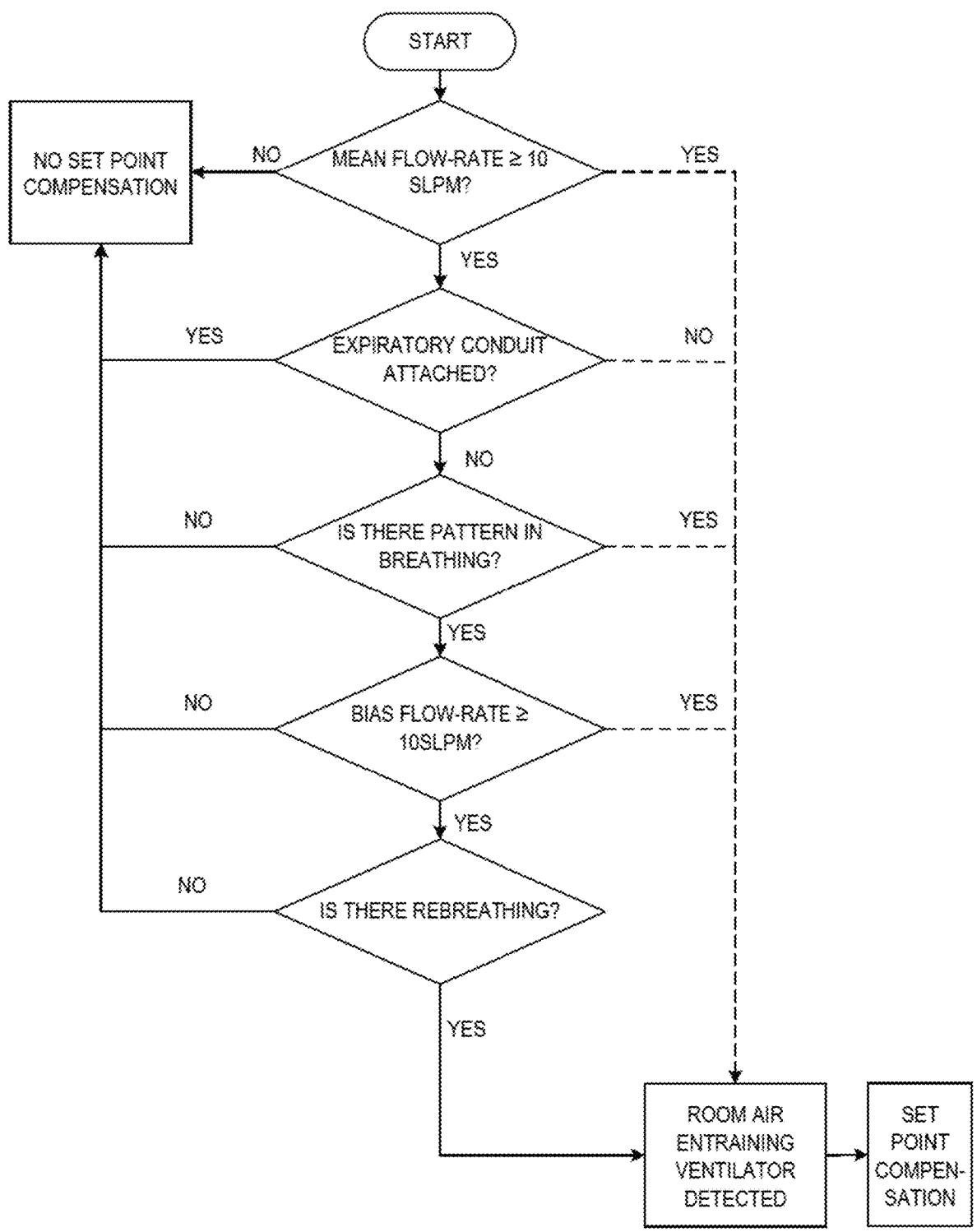
FIG. 10D illustrates a flow chart of a method for respiratory assistance system control according to another embodiment of the present disclosure.

There are multiple approaches for a control system 220 to determine the type of ventilator coupled with the control system 220. In some embodiments, the control system 220 prioritizes the steps discussed above, particularly with respect to FIGS. 10A-10C, and selects the steps that uses less or no additional resources. The resources can include processing power, cost, or other material or design resources. The control system 220 may also prioritize steps that have higher likelihood of identifying the system conditions without requiring additional measurements. In some embodiments, when system conditions are not apparent or there is low confidence associated with the measurements, the control system 220 can perform additional steps to identify system conditions with sufficient confidence. FIG. 10D illustrates another embodiment of a process for determination of a whether a room air entrained or non-entrained ventilator is coupled with the control system 220. As illustrated with respect to the dotted lines, the steps shown in FIG. 10D that correspond to 10A as discussed above can be performed selectively in different combination and, out of order by the control system 220. Accordingly, the steps illustrated in FIG. 10D can be used in any combination or be operated by the control system 220 as an "or" logical operator. In some embodiments, the control system 220 may select a single block shown in FIG. 10D to determine whether a room air entrained or non entrained ventilator is coupled with the control system 220. The methods for the respective blocks are discussed above with respect to FIG. 10A.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

PREFERRED FEATURES

1. A respiratory assistance system for delivery of heated and humidified gases to a patient via a patient interface from a gases source through an inspiratory conduit and a humidification chamber, the respiratory assistance system comprising:
   a chamber heater configured to heat and humidify a flow of respiratory gases; and
   a controller comprising one or more hardware processors configured to:
      determine one or more characteristics of respiratory gases; and
      determine a type of gases source based on the determined characteristic of respiratory gases.

2. The respiratory assistance system of clause 1, further comprising a patient interface configured to deliver a flow of respiratory gases received from a gases source.

3. The respiratory assistance system of any of the preceding clauses, further comprising an inspiratory conduit configured to be in fluid communication with the patient interface and the gases source.

4. The respiratory assistance system of any of the preceding clauses, further comprising a humidification chamber comprising a chamber inlet, a chamber outlet, and a gases flow path between the chamber inlet and the chamber outlet, the chamber inlet configured to be in fluid communication with the gases source and the chamber outlet configured to be in fluid communication with the inspiratory conduit, the humidification chamber configured to hold a volume of liquid.

5. The respiratory assistance system of any of the preceding clauses, wherein the controller is further configured to control a set point temperature associated with the chamber heater based on the determined type of gases source.

6. The respiratory assistance system of any of the preceding clauses, wherein the controller is further configured to generate an indicator corresponding to the determined type of gases source for communication to a user.

7. The respiratory assistance system of clause 5 or clause 6 when depending on clause 5, wherein said control the set point temperature comprises modifying a representation of the set point temperature in a hardware memory.

8. The respiratory assistance system of clause 5 or any one of clauses 6-7 when depending on clause 5, wherein the controller is further configured to lower the set point temperature based on the determination of the type of gases source to be an air entraining gases source.

9. The respiratory assistance system of any of the preceding clauses, wherein the controller is further configured to increase the set point temperature based on the determination of the type of gases source to be an air entraining gases source.

10. The respiratory assistance system of clause 5 or any one of clauses 6-9 when depending on clause 5, wherein the controller is further configured to generate an indicator corresponding to the set point temperature for communication to a user.

11. The respiratory assistance system of any of the preceding clauses, wherein the characteristic of respiratory gases comprises at least one of: a mean flow rate, a breathing pattern, a bias flow rate, a reverse flow detection, a rebreathing detection.

12. The respiratory assistance system of any of the preceding clauses, wherein said determination of the type of gases source further comprises detecting a hardware component attached to the humidification chamber.

13. The respiratory assistance system of clause 12, wherein the hardware component is an expiratory circuit or an expiratory conduit.

14. The respiratory assistance system of clause 13, wherein the detection of the expiratory circuit is based on a characteristic signal comprising at least one of: a voltage measurement, or an impedance measurement, or a resistance measurement.

15. The respiratory assistance system of any of the preceding clauses, wherein said determination of the type of gases source further comprises detecting a behaviour of the flow of respiratory gases based on the determined one or more characteristics of the respiratory gases.

16. The respiratory assistance system of clause 15, wherein the behaviour comprises a detection of a breathing pattern, a detection of bias flow, or a detection of rebreathing.

17. The respiratory assistance system of clause 16, wherein the detection of the breathing pattern comprises monitoring flow movements or pressure changes and comparing the monitored flow movements or pressure changes with a threshold.

18. The respiratory assistance system of clause 16 or 17, wherein the detection of bias flow comprises measuring a raw flow measurement from a flow sensor and comparing the raw flow measurement with a bias threshold.

19. The respiratory assistance system of any of the preceding clauses, wherein the determination of the type of gases source comprises comparing a bias flow rate with a mean flow rate.

20. The respiratory assistance system of clause 19, wherein the controller is configured to determine the bias flow rate based on a rate of change of flow.

21. The respiratory assistance system of clause 19 or 20, wherein the controller is configured to determine the bias flow rate by deriving a rate of change of flow from flow rate measurements, determining an average flow, and performing a first check to confirm a bias flow, wherein the first check involves determining if the rate of change is 0 and the flow is less than the average flow.

22. The respiratory assistance system of any of clauses 16-21, wherein the detection of rebreathing comprises determining a flow profile detected at an outlet flow sensor and an inlet flow sensor; and comparing the flow profiles with a predetermined flow profile.

23. The respiratory assistance system of any of clauses 16-21, wherein the detection of rebreathing comprises extracting a first flow profile at an inlet flow sensor and a second flow profile at an outlet flow sensor; and comparing the first flow profile with the second flow profile.

24. The respiratory assistance system of any of clauses 16-21, wherein the detection of rebreathing comprises detecting an inspiratory phase and an expiratory phase; and comparing a length of the expiratory phase with a length of the inspiratory phase.

25. The respiratory assistance system of any of clauses 16-21, wherein the detection of rebreathing comprises correlating an inspiratory phase breathing pattern with an expiratory phase breathing pattern.

26. The respiratory assistance system of any of the preceding clauses, further comprising an inlet temperature sensor; wherein the one or more characteristics of respiratory gases comprises a temperature measurement from the inlet temperature sensor, and wherein the controller is configured to determine the type of gases source based on comparing the temperature measurement from the inlet sensor with one or more thresholds.

27. The respiratory assistance system of clause 26, wherein an inlet temperature less than the threshold denotes a non air entraining ventilator, and an inlet gases temperature greater than the threshold denotes an air entraining ventilator.

28. A respiratory assistance system comprising:
a controller comprising one or more hardware processors and a memory; and
a chamber heater;
wherein the controller is configured to:
detect a rebreathing flow pattern;
determine a gases source or an operating condition based on the detection of the rebreathing flow pattern; and
control an operating parameter based corresponding to the chamber heater on the determination of the gases source.

29. The respiratory assistance system of clause 28, wherein the detection of the rebreathing flow pattern further comprises correlating measurements from an inlet sensor and an outlet sensor.

30. The respiratory assistance system of clause 29, wherein the inlet sensor and the outlet sensor comprise one or more flow sensors configured to detect a flow pattern or flow signal, and wherein the detection of the rebreathing flow pattern comprises correlating the flow pattern or flow signal.

31. The respiratory assistance system of any of clauses 28-30, wherein the operating parameter is a chamber outlet temperature set point.

32. The respiratory assistance system of clause 30 or 31, wherein the flow pattern or flow signal comprises one or more power dissipation values, and wherein the one or more flow sensors comprise a heated bead flow sensor.

33. The respiratory assistance system of any of clauses 28-32, wherein the gases source comprises an air entraining ventilator or a non-air entraining ventilator.

34. A controller comprising one or more hardware processors coupled to a respiratory assistance system, the controller configured to automatically determine a configuration of the respiratory assistance system, the controller comprising:
a hardware memory;
a user interface configured to receive an input from a user; and
one or more hardware processors coupled to a plurality of hardware components of the respiratory assistance system;
wherein the one or more hardware processors are configured to detect the received user input and automatically confirm the operational configuration of the system matches the received user input based on one or more sensor inputs from at least one sensor or the hardware components.

35. The controller of clause 34, wherein the one or more hardware processors are configured to select a default mode based on no input received from the user.

36. The controller of clause 34 or 35, wherein the one or more hardware processors are configured to select a safety mode prior to confirmation of the operational configuration.

37. The controller of any of clauses 34-36, wherein the one or more hardware processors are configured to control a heater plate temperature of a heater plate based on a first temperature measurement from the outlet temperature sensor and a second temperature measurement corresponding to the outlet temperature set point.

38. A respiratory assistance system for delivery of heated and humidified gases to a patient, the respiratory assistance system comprising:
a gas source configured to provide a flow of respiratory gases;
a patient interface configured to deliver the flow of respiratory gases to the patient;
an inspiratory conduit configured to be in fluid communication with the patient interface;
a humidification chamber configured to hold a volume of liquid, the humidification chamber including a chamber inlet, a chamber outlet, and a gases flow path between the chamber inlet and the chamber outlet, the chamber inlet configured to be in fluid communication with the gas source and the chamber outlet configured to be in fluid communication with the inspiratory conduit;
a chamber heater configured to heat the volume of liquid and the flow of respiratory gases in the gases flow path within the humidification chamber so as to heat and humidify the flow of respiratory gases; and
a controller configured to:
determine a gases characteristic of the flow of respiratory gases provided by the gas source;
determine whether to change a first temperature, based at least in part on the determined gases characteristic; and
determine an amount of power to provide to the chamber heater, based at least in part on the determined gases characteristic and at least in part on the first temperature.

39. The respiratory assistance system of clause 38, further comprising a flow rate sensor, wherein said controller is further configured to change the first temperature based at least in part on a measurement from the flow rate sensor.

40. The respiratory assistance system of clause 38 or 39, wherein said controller is further configured to:
  detect a signal from a heating element corresponding to an expiratory conduit; and
  change the first temperature based at least in part on the detected signal.

41. The respiratory assistance system of any of clauses 38-40, wherein the controller is further configured to:
  receive user input from a display; and
  change the first temperature based at least in part on the user input.

42. The respiratory assistance system of any of clauses 38-41, further comprising a temperature sensor, wherein the controller is further configured to:
  receive a measurement from the temperature sensor; and
  change the first temperature based at least in part on the received measurement from the temperature sensor.

43. The respiratory assistance system of any of clauses 38-42, further comprising a humidity sensor, wherein the controller is further configured to:
  receive a measurement from the humidity sensor; and
  change the first temperature based at least in part on the received measurement from the humidity sensor.

44. A respiratory assistance system configured to automatically determine which of a plurality of optional configuration components and settings are used with the respiratory assistance system, the system comprising:
  a plurality of optional hardware components, wherein each component is configured to be connectable with the respiratory assistance system; and
  a hardware processor configured to analyse operational characteristics based on one more inputs from at least one sensor or optional hardware component attachments and determine a desired operational configuration based on the analysis.

45. A respiratory assistance system configured to automatically determine which of a plurality of optional configuration components and settings are used with the respiratory assistance system, the system comprising:
  a plurality of optional hardware components, wherein each component is configured to be connectable with the respiratory assistance system;
  a user interface configured to receive an input from a user; and
  a hardware processor configured to detect the received user input and automatically confirm that an operational configuration of the respiratory assistance system matches with the received user input based on one more inputs from at least one sensor or optional hardware component attachments.

46. The respiratory assistance system of clause 45, wherein at least one of the optional hardware components comprises an expiratory heater wire.

47. The respiratory assistance system of clause 46, wherein the hardware processor is configured to detect a signal characteristic from the expiratory heater wire to determine a status of connection of the expiratory heater wire.

48. The respiratory assistance system of clause 47, wherein the signal characteristic comprises at least one of a voltage measurement or a resistance measurement.

49. A method for determining a type of gases source comprising: determining one or more characteristics of respiratory gases; and determining a type of gases source based on the determined characteristics of respiratory gases.

50. The method of clause 49, wherein the method can include any of the features and/or steps of clauses 1 to 48 to determine the characteristics of respiratory gases.

51. A respiratory assistance system for delivery of heated and humidified gases to a patient, the respiratory assistance system comprising:
  a patient interface configured to deliver a flow of respiratory gases received from a gases source;
  an inspiratory conduit configured to be in fluid communication with the patient interface and the gases source;
  a humidification chamber comprising a chamber inlet, a chamber outlet, and a gases flow path between the chamber inlet and the chamber outlet, the chamber inlet configured to be in fluid communication with the gases source and the chamber outlet configured to be in fluid communication with the inspiratory conduit, the humidification chamber configured to hold a volume of liquid;
  a chamber heater configured to heat the volume of liquid and the flow of respiratory gases in the gases flow path within the humidification chamber so as to heat and humidify the flow of respiratory gases; and
  a controller comprising one or more hardware processors configured to:
    determine one or more characteristics of respiratory gases; and
    determine a type of gases source based on the determined characteristic of respiratory gases.

52. The respiratory assistance system of clause 51, wherein the method of clause 49 is configured to utilize any of the features of clauses 1 to 48.

What is claimed is:

1. A respiratory assistance system for delivery of heated and humidified gases to a patient via a patient interface from a gases source through an inspiratory conduit and a humidification chamber, the respiratory assistance system comprising:
  a chamber heater configured to heat and humidify a flow of respiratory gases; and
  a controller comprising one or more hardware processors configured to:
    determine one or more characteristics of respiratory gases; and
    determine a type of gases source based on the determined characteristic of respiratory gases;
  the controller being further configured to control a set point temperature associated with the chamber heater based on the determined type of gases source.

2. The respiratory assistance system of claim 1, further comprising a patient interface configured to deliver a flow of respiratory gases received from a gases source.

3. The respiratory assistance system of claim 1, further comprising an inspiratory conduit configured to be in fluid communication with the patient interface and the gases source.

4. The respiratory assistance system of claim 1, further comprising a humidification chamber comprising a chamber inlet, a chamber outlet, and a gases flow path between the chamber inlet and the chamber outlet, the chamber inlet configured to be in fluid communication with the gases source and the chamber outlet configured to be in fluid communication with the inspiratory conduit, the humidification chamber configured to hold a volume of liquid.

5. The respiratory assistance system of claim 1, wherein the controller is further configured to generate an indicator corresponding to the determined type of gases source for communication to a user.

6. The respiratory assistance system of claim 1, wherein said control the set point temperature comprises modifying a representation of the set point temperature in a hardware memory.

7. The respiratory assistance system of claim 1, wherein the controller is further configured to lower the set point temperature based on the determination of the type of gases source to be an air entraining gases source.

8. The respiratory assistance system of claim 1, wherein the controller is further configured to increase the set point temperature based on the determination of the type of gases source to be an air entraining gases source.

9. The respiratory assistance system of claim 1, wherein the controller is further configured to generate an indicator corresponding to the set point temperature for communication to a user.

10. The respiratory assistance system of claim 1, wherein the characteristic of respiratory gases comprises at least one of: a mean flow rate, a breathing pattern, a bias flow rate, a reverse flow detection, a rebreathing detection.

11. The respiratory assistance system of claim 10, wherein the hardware component is an expiratory circuit or an expiratory conduit.

12. The respiratory assistance system of claim 1, wherein said determination of the type of gases source further comprises detecting a hardware component attached to the humidification chamber.

13. The respiratory assistance system of claim 12, wherein the detection of the expiratory circuit is based on a characteristic signal comprising at least one of: a voltage measurement, or an impedance measurement, or a resistance measurement.

14. The respiratory assistance system of claim 13, wherein the behaviour comprises a detection of a breathing pattern, a detection of bias flow, or a detection of rebreathing.

15. The respiratory assistance system of claim 13, wherein said determination of the type of gases source further comprises detecting a behaviour of the flow of respiratory gases based on the determined one or more characteristics of the respiratory gases.

16. The respiratory assistance system of claim 15, wherein the detection of the breathing pattern comprises monitoring flow movements or pressure changes and comparing the monitored flow movements or pressure changes with a threshold.

17. The respiratory assistance system of claim 15, wherein the determination of the type of gases source comprises comparing a bias flow rate with a mean flow rate.

18. The respiratory assistance system of claim 15, wherein the detection of rebreathing comprises determining a flow profile detected at an outlet flow sensor and an inlet flow sensor; and comparing the flow profiles with a predetermined flow profile.

19. The respiratory assistance system of claim 15, wherein the detection of rebreathing comprises extracting a first flow profile at an inlet flow sensor and a second flow profile at an outlet flow sensor; and comparing the first flow profile with the second flow profile.

20. The respiratory assistance system of claim 15, wherein the detection of rebreathing comprises detecting an inspiratory phase and an expiratory phase; and comparing a length of the expiratory phase with a length of the inspiratory phase.

21. The respiratory assistance system of claim 15, wherein the detection of rebreathing comprises correlating an inspiratory phase breathing pattern with an expiratory phase breathing pattern.

22. The respiratory assistance system of claim 15, wherein the detection of bias flow comprises measuring a raw flow measurement from a flow sensor and comparing the raw flow measurement with a bias threshold.

23. The respiratory assistance system of claim 13, wherein the controller is configured to determine the bias flow rate based on a rate of change of flow.

24. The respiratory assistance system of claim 22, wherein the controller is configured to determine the bias flow rate by deriving a rate of change of flow from flow rate measurements, determining an average flow, and performing a first check to confirm a bias flow, wherein the first check involves determining if the rate of change is 0 and the flow is less than the average flow.

25. The respiratory assistance system of claim 15, further comprising an inlet temperature sensor; wherein the one or more characteristics of respiratory gases comprises a temperature measurement from the inlet temperature sensor, and wherein the controller is configured to determine the type of gases source based on comparing the temperature measurement from the inlet sensor with one or more thresholds.

26. The respiratory assistance system of claim 25, wherein an inlet temperature less than the threshold denotes a non air entraining ventilator, and an inlet gases temperature greater than the threshold denotes an air entraining ventilator.

\* \* \* \* \*

UNITED STATES PATENT AND TRADEMARK OFFICE
CERTIFICATE OF CORRECTION

PATENT NO. : 10,905,843 B2  
APPLICATION NO. : 16/070516  
DATED : February 2, 2021  
INVENTOR(S) : Daniel John Smith et al.

It is certified that error appears in the above-identified patent and that said Letters Patent is hereby corrected as shown below:

In Column 34, Line 26, in Claim 23, delete "13," and insert --22,--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*